(12) United States Patent
Noji

(10) Patent No.: US 9,801,555 B2
(45) Date of Patent: Oct. 31, 2017

(54) THORACIC DIAGNOSIS ASSISTANCE SYSTEM

(71) Applicant: Konica Minolta, Inc., Tokyo (JP)

(72) Inventor: Sho Noji, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 377 days.

(21) Appl. No.: 14/471,094

(22) Filed: Aug. 28, 2014

(65) Prior Publication Data

US 2015/0065817 A1    Mar. 5, 2015

(30) Foreign Application Priority Data

Aug. 28, 2013  (JP) ................................ 2013-176971

(51) Int. Cl.
*G06K 9/00*   (2006.01)
*A61B 5/026*  (2006.01)
(Continued)

(52) U.S. Cl.
CPC .............. *A61B 5/026* (2013.01); *A61B 5/113* (2013.01); *A61B 6/5264* (2013.01); *G06T 5/006* (2013.01); *G06T 7/11* (2017.01); *A61B 5/743* (2013.01); *A61B 6/461* (2013.01); *A61B 6/486* (2013.01); *A61B 6/507* (2013.01); *A61B 6/5217* (2013.01); *A61B 6/54* (2013.01); *A61B 6/563* (2013.01); *G06T 2207/10116* (2013.01); *G06T 2207/20101* (2013.01); *G06T 2207/30061* (2013.01)

(58) Field of Classification Search
CPC ....... A61B 5/026; A61B 6/5264; A61B 5/743; A61B 6/461; A61B 6/486; A61B 6/507; A61B 6/54; A61B 6/563; G06T 5/006; G06T 7/0081; G06T 2207/10116; G06T 2207/20101; G06T 2207/30061
See application file for complete search history.

(56) References Cited

U.S. PATENT DOCUMENTS 5,065,348 A * 11/1991 Kuragano ............... G06T 17/20
                                                          345/419
7,817,828 B2 * 10/2010 Miyazaki .............. G06F 19/321
                                                          382/128
(Continued)

FOREIGN PATENT DOCUMENTS

JP      2009153677 A    7/2009
WO      200707812 A1    7/2007

*Primary Examiner* — Amara Abdi
(74) *Attorney, Agent, or Firm* — Cantor Colburn LLP

(57) ABSTRACT

According to one implementation, the system includes, a capturing unit, a deforming unit, and a generating unit. The capturing unit captures a dynamic state of a thoracic portion to generate a plurality of frame images. The deforming unit sets a reference point in a position corresponding to each other among the plurality of generated frame images. The deforming unit extracts a lung field region from each of the frame images. The deforming unit deforms a shape of the lung field region so that a distance from the set reference point to an outline of an outer side of the lung field region becomes a certain distance. The generating unit analyzes a dynamic state in the lung field region and generates an analysis result image showing a result of the analysis in a corresponding position in the deformed lung field region.

16 Claims, 15 Drawing Sheets

(51) Int. Cl.
*A61B 5/113* (2006.01)
*G06T 5/00* (2006.01)
*G06T 7/11* (2017.01)
A61B 5/00 (2006.01)
A61B 6/00 (2006.01)

(56) References Cited

U.S. PATENT DOCUMENTS

| | | | | |
|---|---|---|---|---|
| 2003/0190064 | A1* | 10/2003 | Inoue | A61B 6/02 382/128 |
| 2009/0097731 | A1* | 4/2009 | Sanada | A61B 5/0205 382/132 |
| 2010/0094133 | A1* | 4/2010 | Yoshiara | A61B 8/08 600/453 |
| 2013/0083982 | A1* | 4/2013 | Nakamura | G06T 7/149 382/128 |

* cited by examiner

SMALL ◄──► LARGE
MAXIMUM AIR VELOCITY

SMALL ◄──► LARGE
MAXIMUM AIR VELOCITY

SMALL ◄──► LARGE
MAXIMUM AIR VELOCITY RATIO

THORACIC DIAGNOSIS ASSISTANCE SYSTEM

CROSS REFERENCE

The present invention claims priority under 35 U.S.C. §119 to Japanese Application No. 2013-176971 filed Aug. 28, 2013, the entire content of which is incorporated herein by reference.

BACKGROUND

Field of the Invention

The present invention relates to a thoracic diagnosis assistance system.

Description of Related Art

Instead of stationary image capturing and diagnosis by thoracic radiation using a conventional film/screen or photostimulable phosphor plate, there is an approach to capture a thoracic dynamic state image using a semiconductor image sensor such as an FPD (flat panel detector), etc., to be applied to diagnosis. Specifically, fast responsiveness of reading and deleting of image data of the semiconductor image sensor is used and pulsed radiation is successively irradiated from a radiation source to match with the timing of reading and deleting by the semiconductor image sensor to perform capturing a plurality of times in one second. With this, a thoracic dynamic state is captured. A string of plurality of frame images obtained by capturing are sequentially displayed and it is possible for a physician to observe a string of movement of a chest portion according to breath movement, heartbeat, etc.

Various techniques are proposed to analyze ventilation and blood flow of lungs based on a thoracic dynamic state image.

For example, there is proposed a technique of judging whether ventilation capacity of the lungs is normal or abnormal for each region of an image capturing the thoracic dynamic state, and displaying on a display unit information regarding a position and name of an anatomical structure judged to be abnormal (For example, see Japanese Patent Application Laid-Open Publication No. 2009-153677).

For example, there is proposed a technique of calculating a pixel value in a predetermined range for each frame image composing the thoracic dynamic state image, and generating a temporal change amount of the calculated pixel value as information of pulmonary blood flow (For example, see pamphlet of WO 2007/078012).

However, a shape of a lung field or a stream of a blood vessel in a lung field in the thoracic dynamic state image is different for each individual or depending on the state when the dynamic state image is captured. Therefore, for example, there is a problem that it is not easy to use the thoracic dynamic state image as is for diagnosis by a physician, comparison analysis with image of other individuals, comparison analysis with past images of a same patient, blood flow analysis specifying a position of a blood vessel, etc.

SUMMARY

The present invention has been made in consideration of the above problems, and it is one of main objects to provide an image with which a lung field can be easily analyzed and diagnosed.

In order to achieve at least one of the above-described objects, according to an aspect of the present invention, there is provided a thoracic diagnosis assistance system including:

a capturing unit which captures a dynamic state of a thoracic portion to generate a plurality of frame images;

a deforming unit which sets a reference point in a position corresponding to each other among the plurality of generated frame images, extracts a lung field region from each of the plurality of frame images, and deforms a shape of the lung field region in each of the plurality of frame images so that a distance from the set reference point to an outline of an outer side of the lung field region becomes a certain distance; and a generating unit which analyzes a dynamic state in the lung field region based on the plurality of frame images in which a shape of the lung field region is deformed by the deforming unit, and generates an analysis result image showing a result of the analysis in a corresponding position in the deformed lung field region.

According to another aspect of the present invention, there is provided a thoracic diagnosis assistance system including:

a capturing unit which captures a dynamic state of a thoracic portion to generate a plurality of frame images;

a generating unit which extracts a lung field region from the plurality of generated frame images, analyzes a dynamic state in the lung field region, and generates an analysis result image showing a result of the analysis in a corresponding position in the lung field region; and a deforming unit which sets a reference point in the analysis result image, and deforms a shape of the lung field region in the analysis result image so that a distance from the set reference point to an outline of an outer side of the lung field region in the analysis result image becomes a certain distance.

According to the present invention, it is possible to provide an image with which a lung field can be easily analyzed and diagnosed.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

An embodiment of the present invention is described in detail with reference to the drawings. However, the scope of the claims is not limited to the illustrated examples.

[First Embodiment]

[Configuration of Thoracic Diagnosis Assistance System 100]

First, the configuration is described.

Figure 1:
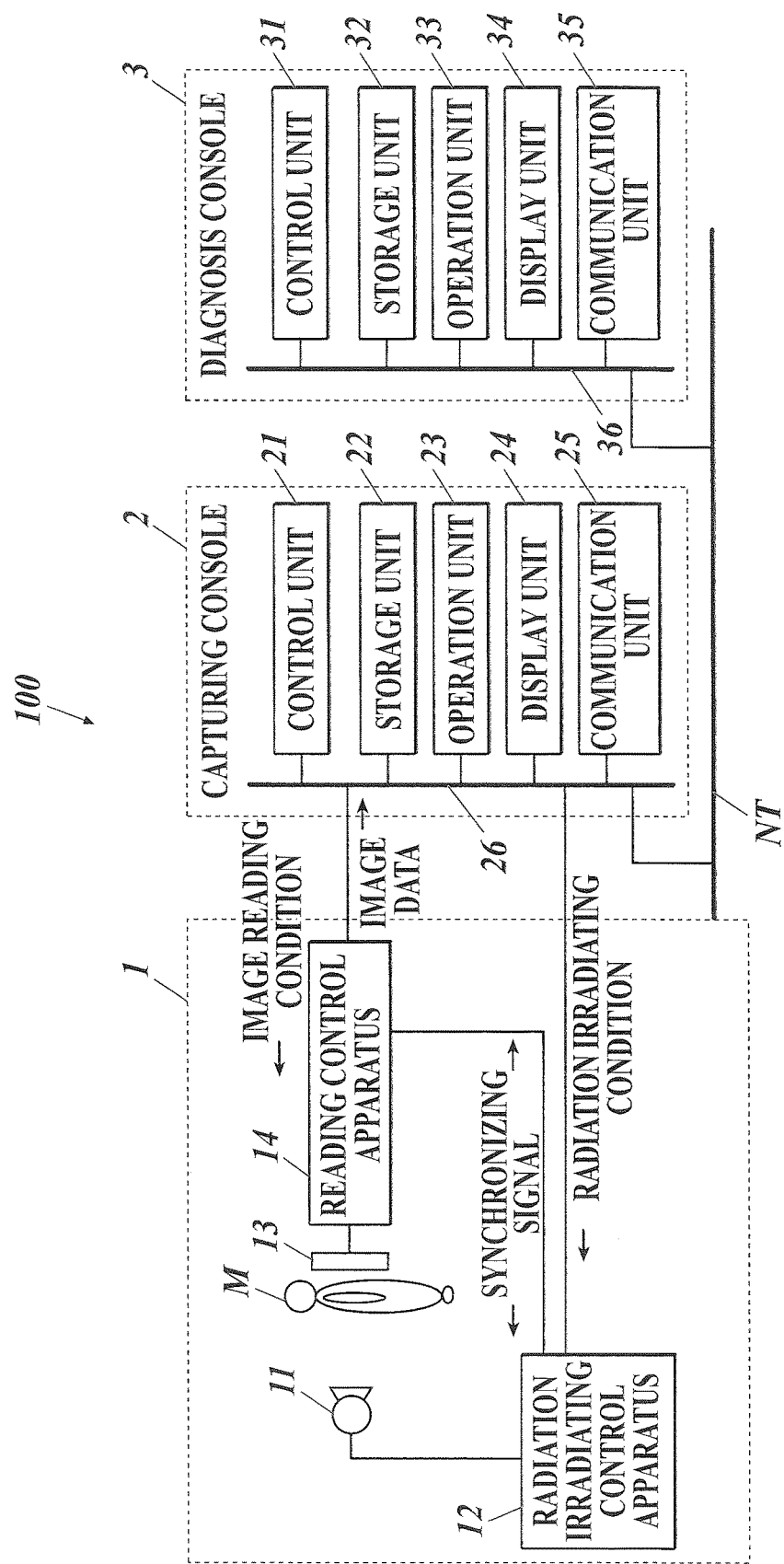
FIG. 1 is a diagram showing an entire configuration of a thoracic diagnosis assistance system of an embodiment of the present invention.

FIG. 1 shows an entire configuration of a thoracic diagnosis assistance system 100 of the present embodiment.

As shown in FIG. 1, the thoracic diagnosis assistance system 100 is configured by connecting a capturing apparatus 1 with a capturing console 2 through a communication cable, etc. and connecting a capturing console 2 with a diagnosis console 3 through a communication network NT such as a LAN (Local Area Network), etc. Each apparatus composing the thoracic diagnosis assistance system 100 complies with a DICOM (Digital Image and Communications in Medicine) standard, and communication between the apparatuses are performed according to DICOM.

[Configuration of Capturing Apparatus 1]

The capturing apparatus 1 is a capturing unit to capture a state of the chest portion moving in cycles, such as change in shape from expansion and contraction of the lungs according to breathing movement, heartbeat, and the like. The dynamic state capturing is performed by successively irradiating radiation such as X-rays on a chest portion of a human body to obtain a plurality of images (in other words, successive capturing). A string of images obtained by successive capturing is called a dynamic state image. Each of the plurality of images which compose the dynamic state image is called a frame image.

As shown in FIG. 1, the capturing apparatus 1 includes a radiation source 11, a radiation irradiating control apparatus 12, a radiation detecting unit 13, a reading control apparatus 14, and the like.

The radiation source 11 is provided in a position facing the radiation detecting unit 13 with a subject M in between. According to control of the radiation irradiating control apparatus 12, the radiation source 11 irradiates radiation (X-ray) on the subject M.

The radiation irradiating control apparatus 12 is connected to the capturing console 2 and the radiation irradiating control apparatus 12 controls the radiation source 11 to perform radiation capturing based on radiation irradiating conditions input from the capturing console 2. The radiation irradiating conditions input from the capturing console 2 are, for example, pulse rate, pulse width, and pulse interval of successive irradiating, number of captured frames for each capturing, X-ray tube current value, X-ray tube voltage value, filter type, etc. The pulse rate is the number of times the radiation is irradiated in one second and matches with a later described frame rate. The pulse width is the amount of time the radiation is irradiated each time the radiation is irradiated. The pulse interval is the amount of time from when a certain irradiating of the radiation starts to when the next irradiating of the radiation starts in successive capturing. The pulse interval matches with a later described frame interval.

The radiation detecting unit 13 is composed of a semiconductor image sensor such as a FPD, etc. The FPD includes, for example, a glass substrate, etc. In the FPD, a plurality of detecting elements (pixels) are arranged in a matrix shape in a predetermined position on the substrate. The pixels detect radiation which is irradiated from the radiation source 11 and which passes through at least the subject M according to intensity, and converts the detected radiation into electric signals to be accumulated in the detecting elements. Each pixel is composed of a switching unit such as a TFT (Thin Film Transistor), etc. As the FPD, there is an indirect conversion type which converts an X-ray to an electric signal with a photoelectric conversion element through a scintillator or a direct conversion type which directly converts the X-ray to the electric signal, and either type can be applied to the present embodiment.

The radiation detecting unit 13 is provided in a position facing the radiation source 11 with the subject M in between.

The reading control apparatus 14 is connected to the capturing console 2. The reading control apparatus 14 controls the switching unit of each pixel of the radiation detecting unit 13 based on image reading conditions input from the capturing console 2, switches reading of electric signals accumulated in each pixel, and reads the electric signals accumulated in the radiation detecting unit 13 to obtain image data. The image data is the frame image. Then, the reading control apparatus 14 outputs the obtained frame image to the capturing console 2. The image reading conditions are, for example, frame rate, frame interval, pixel size, image size (matrix size), and the like. The frame rate is the number of frame images obtained in one second and matches with the pulse rate. The frame interval is the amount of time from when a certain operation of obtaining a frame image starts to when the operation of obtaining the next frame image starts in successive capturing. The frame interval matches with the pulse interval.

Here, the radiation irradiating control apparatus 12 and the reading control apparatus 14 are connected to each other and the apparatuses transmit synchronizing signals between each other to synchronize the radiation irradiating operation with the image reading operation.

[Configuration of Capturing Console 2]

The capturing console 2 outputs the radiation irradiating condition and the image reading condition to the capturing apparatus 1 and controls the radiation capturing and the reading operation of the radiation image by the capturing apparatus 1. The capturing console 2 also displays the dynamic state image obtained by the capturing apparatus 1 so that the capturing operator can confirm positioning or confirm whether or not the image is suitable for diagnosis.

As shown in FIG. 1, the capturing console 2 includes a control unit 21, a storage unit 22, an operation unit 23, a display unit 24, and a communication unit 25 and each unit is connected to each other through a bus 26.

The control unit 21 includes a CPU (Central Processing Unit), a RAM (Random Access Memory), and the like. According to operation on the operation unit 23, the CPU of the control unit 21 reads a system program and various processing programs stored in the storage unit 22 to be expanded in the RAM, and performs various processing such as later described capturing control processing according to the expanded program to centrally control operation of each unit of the capturing console 2 and radiation irradiating operation and reading operation of the capturing apparatus 1.

The storage unit 22 includes a nonvolatile semiconductor memory, a hard disk and the like. The storage unit 22 stores various programs performed by the control unit 21, parameters necessary to perform processing by the program, or data of the processing result, etc. For example, the storage unit 22 stores a program to perform the capturing control processing shown in FIG. 2. The storage unit 22 stores the radiation irradiating conditions and the image reading conditions associated with the examination target site. Various programs are stored in a state of a readable program code, and the control unit 21 sequentially performs the operation according to the program code.

The operation unit 23 is composed of a keyboard including a cursor key, a numeral input key, various function keys, etc., and a pointing device such as a mouse, etc. The operation unit 23 outputs to the control unit 21 instruction signals input by key operation on the keyboard or mouse operation. The operation unit 23 can include a touch panel on the display screen of the display unit 24, and in this case, the operation unit 23 outputs to the control unit 21 instruction signals input through the touch panel.

The display unit 24 is configured with a monitor such as an LCD (Liquid Crystal Display), a CRT (Cathode Ray Tube) and the like. According to an instruction of display signals input from the control unit 21, the display unit 24 displays input instructions from the operation unit 23, data and the like.

The communication unit 25 includes a LAN adaptor, modem, a TA (Terminal Adapter), etc., and controls transmitting and receiving of data between the apparatuses connected to the communication network NT.

[Configuration of Diagnosis Console 3]

The diagnosis console 3 is a dynamic state image processing apparatus which obtains a dynamic state image from the capturing console 2, and displays the obtained dynamic state image so that the image is used for diagnosis by a physician.

As shown in FIG. 1, the diagnosis console 3 includes a control unit 31, a storage unit 32, an operation unit 33, a display unit 34, and a communication unit 35, and each unit is connected to each other through a bus 36.

The control unit 31 includes a CPU (Central Processing Unit), a RAM (Random Access Memory), and the like. According to operation on the operation unit 33, the CPU of the control unit 31 reads a system program and various processing programs stored in the storage unit 32 to be expanded in the RAM, and performs various processing such as later described image analysis processing (image analysis processing A, image analysis processing B) according to the expanded program to centrally control operation of each unit of the diagnosis console 3. The control unit 31 functions as a deforming unit, a generating unit, a display control unit, a region analysis unit, a difference image generating unit, and an extracting unit.

The storage unit 32 includes a nonvolatile semiconductor memory, a hard disk and the like. The storage unit 32 stores various programs performed by the control unit 31 such as a program to perform image analysis processing, parameters necessary to perform processing by the program, or data of the processing result, etc. Various programs are stored in a state of a readable program code, and the control unit 31 sequentially performs the operation according to the program code.

The operation unit 33 is composed of a keyboard including a cursor key, a numeral input key, various function keys, etc., and a pointing device such as a mouse, etc. The operation unit 33 outputs to the control unit 31 instruction signals input by key operation on the keyboard or mouse operation. The operation unit 33 can include a touch panel on the display screen of the display unit 34, and in this case, the operation unit 33 outputs to the control unit 31 instruction signals input through the touch panel.

The display unit 34 is configured with a monitor such as an LCD, a CRT and the like. According to an instruction of display signals input from the control unit 31, the display unit 34 displays input instructions from the operation unit 33, data and the like.

The communication unit 35 includes a LAN adaptor, modem, TA (Terminal Adapter), etc., and controls transmitting and receiving of data between the apparatuses connected to the communication network NT.

[Operation of Thoracic Diagnosis Assistance System 100]

Next, the operation of the thoracic diagnosis assistance system 100 is described.

(Operation of Capturing Apparatus 1, Capturing Console 2)

First, capturing operation by the capturing apparatus 1 and the capturing console 2 is described.

Figure 2:
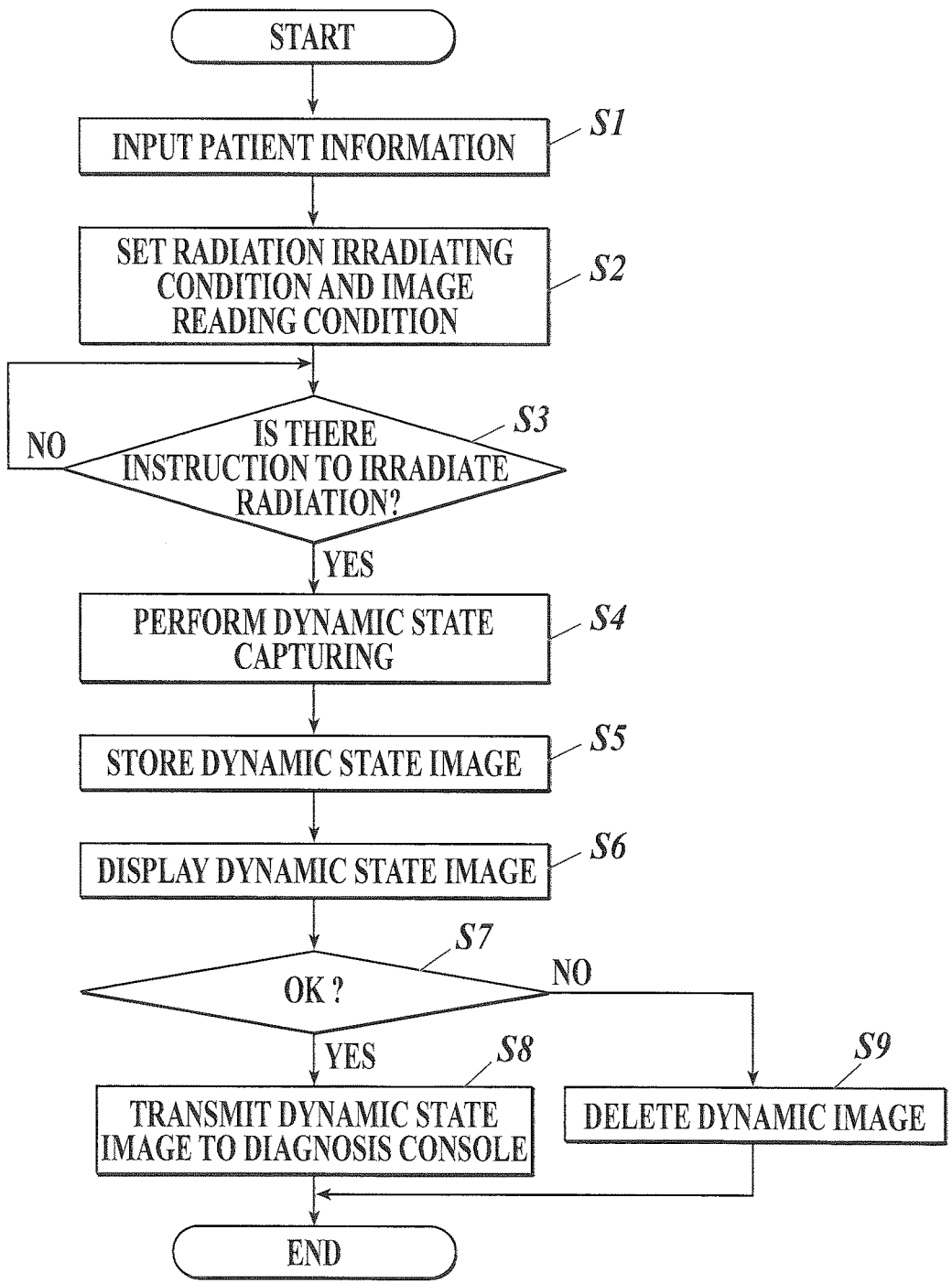
FIG. 2 is a flowchart showing capturing control processing performed by a control unit of a capturing console shown in FIG. 1.

FIG. 2 shows capturing control processing performed by the control unit 21 of the capturing console 2. The capturing control processing is performed by the control unit 21 in coordination with the program stored in the storage unit 22.

First, the capturing operator operates the operation unit 23 of the capturing console 2 and inputs patient information (patient name, height, weight, age, sex, etc.) of a capturing target (subject M) (step S1).

Next, the radiation irradiating condition is read from the storage unit 22 to be set in the radiation irradiating control apparatus 12 and the image reading condition is read from the storage unit 22 to be set in the reading control apparatus 14 (step S2). Here, it is preferable to set the frame rate (pulse rate) to 7.5 frames per second or more, considering the cardiac cycle of a human being. Moreover, it is preferable to set the capturing frame number to a frame number of one cardiac cycle of more Next, the process is put on standby for an instruction of irradiating radiation with the operation of the operation unit 23 (step S3). Here, the one who performs capturing such as the capturing operator instructs the examinee (subject M) to relax to promote resting breathing in order to capture the dynamic state in resting breathing. When the preparation for capturing is complete, the operator operates the operation unit 23 to input the radiation irradiating instruction.

When the radiation irradiating instruction is input on the operation unit 23 (step S3; YES), the capturing start instruction is output to the radiation irradiating control apparatus 12 and the reading control apparatus 14 to start the dynamic state capturing (step S4). In other words, the radiation is irradiated from the radiation source 11 at the pulse interval set in the radiation irradiating control apparatus 12, and the radiation detecting unit 13 obtains the frame image. After capturing of a predetermined number of frames is finished, the control unit 21 outputs an instruction to finish capturing to the radiation irradiating control apparatus 12 and the reading control apparatus 14 and the capturing operation is terminated. The number of frames captured is at least a number of frames to be able to capture one cardiac cycle.

The frame image obtained by capturing is sequentially input to the capturing console 2. Next, each frame image is associated with a number showing an order of capturing to be stored in the storage unit 22 (step S5) and displayed on the display unit 24 (step S6). The capturing operator confirms the positioning, etc. with the displayed dynamic state image, and determines whether an image suitable for diagnosis is obtained by capturing (capturing OK), or capturing needs to be performed again (capturing NG). Then, the operator operates the operation unit 23 and inputs the judging result.

When the judging result showing that capturing is OK is input by the predetermined operation on the operation unit 23 (step S7; YES), an identification ID to identify the dynamic state image, and information such as patient information, examination target site, radiation irradiating conditions, image reading conditions, a number showing capturing order (frame number), and the like are added to each frame image of the string of frame images obtained by the dynamic state capturing (for example, writing in the header region of the image data in a DICOM format) and the frame image is transmitted to the diagnosis console 3 through the communication unit 25 (step S8). Then, the processing ends. When the judging result showing capturing is NG is input by the predetermined operation on the operation unit 23 (step S7; NO), the string of frame images stored in the storage unit 22 is deleted (step S9), and the processing ends.

(Operation of Diagnosis Console 3)

Next, the operation of the diagnosis console 3 is described.

Figure 3:
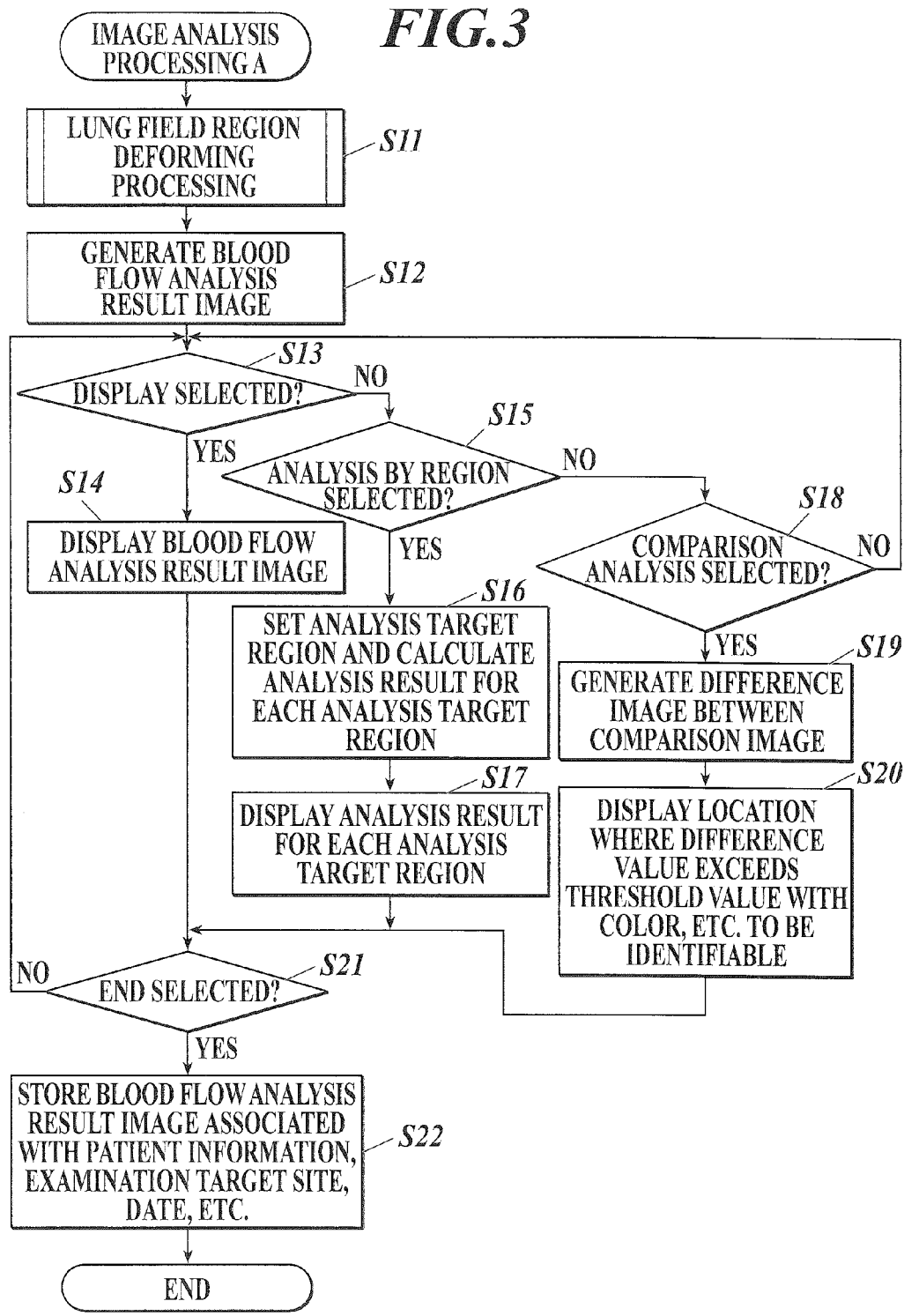
FIG. 3 is a flowchart showing image analysis processing A performed by the control unit of the diagnosis console shown in FIG. 1.

In the diagnosis console 3, when the string of frame images of the dynamic state image is received from the capturing console 2 through the communication unit 35, image analysis processing (image analysis processing A) shown in FIG. 3 is performed by the control unit 31 in coordination with the program stored in the storage unit 32.

The flow of the image analysis processing A is described below with reference to FIG. 3.

First, a lung field region deforming processing is performed on the string of frame images (step S11).

Figure 4:
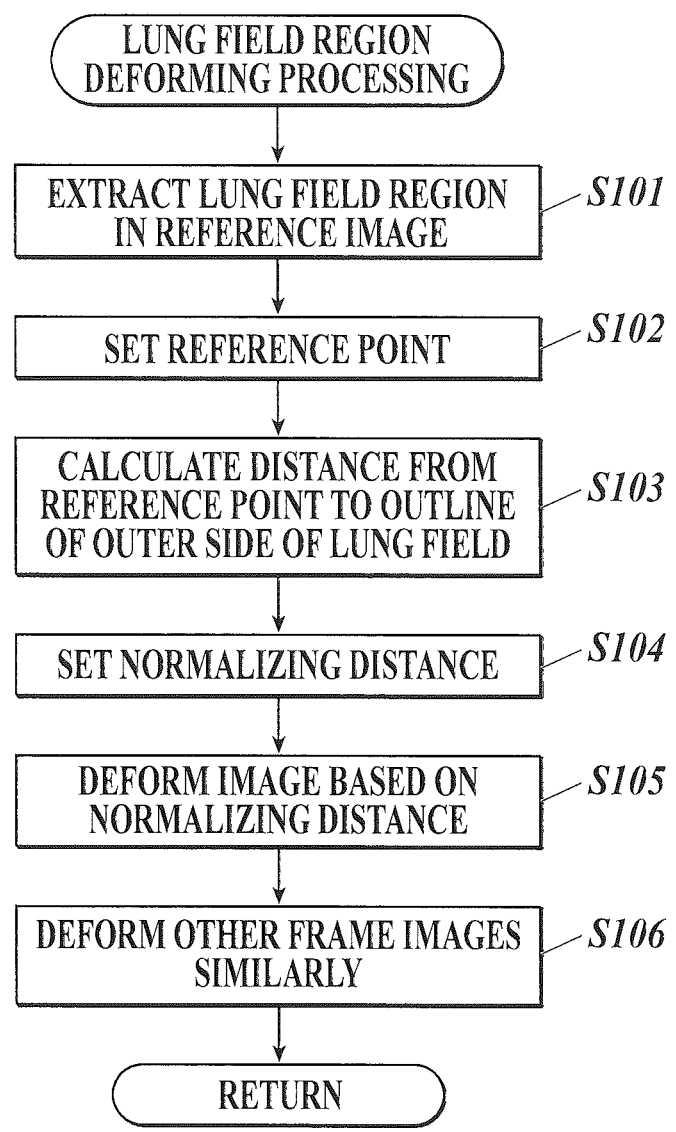
FIG. 4 is a flowchart showing lung field region deforming processing performed in step S11 of FIG. 3.

FIG. 4 shows a flowchart of the lung field region deforming processing.

In the lung field region deforming processing, first, in steps S101 to S105, a shape of a lung field region of one reference image is deformed among the string of frame images, and the deforming similar to the reference image is also performed on the other frame images.

It is preferable to use the frame image of the resting expiration level as the reference image. In resting breathing, the position of the diaphragm becomes highest, in other words, the dimension of the lung field region becomes smallest. Therefore, in the resting expiration level, when a pixel of the reference image is corresponded to a pixel in the same position (coordinates) of another frame image, the region is not corresponded to a region outside the lung field of the frame image. The image of the resting expiration level can be obtained by extracting the image in which the position of the diaphragm (for example, the lower edge section of the lung field region) is highest among the string of frame images.

In step S101 of the image analysis processing A, first the lung field region is extracted from the reference image (step S101).

The method to extract the lung field region can be any method. For example, the threshold value can be obtained by discrimination analysis on the histogram of the signal value (density value) of each pixel of the reference image, and the region with the signal higher than the threshold value is first extracted as the lung field region candidate. Then, edge detecting is performed near a boundary of the lung field region candidate first extracted. If the point where the edge is largest in the small region near the boundary is extracted along the boundary, the boundary of the lung field region can be extracted.

Figure 5A:
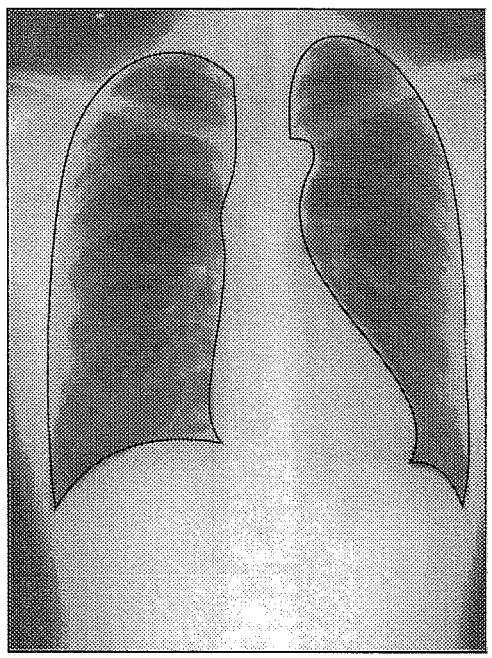
FIG. 5A is a diagram schematically showing extracting a lung field region from a frame image.
Figure 5B:
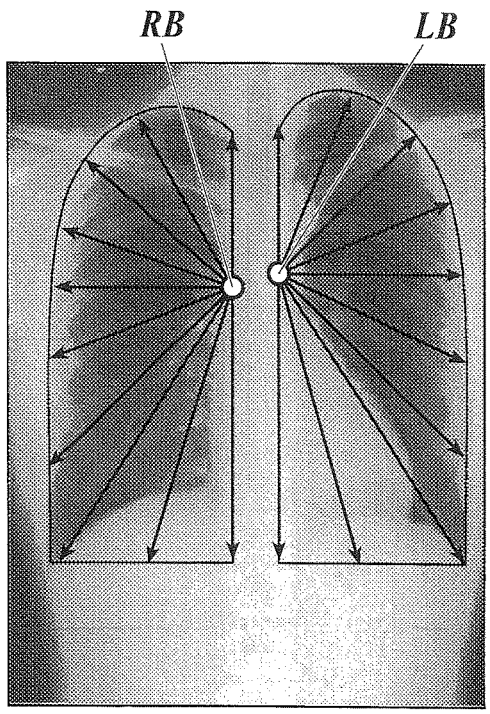
FIG. 5B is a diagram schematically showing a distance from a reference point in a simplified lung field region to an outside of an outline of a lung field region.

In the present embodiment, an outline of a lower edge section of an outline of an outer side and an outline of an inner side of the lung field region (see FIG. 5A) extracted by the above method are simplified to be a straight line in a horizontal direction and vertical direction respectively, and the simplified lung field region is extracted as the lung field region (see FIG. 5B). Position (coordinate) information of the extracted lung field region is stored in the memory of the control unit 31.

Next, a reference point is set from the reference image (step S102). Here, a right pulmonary hilum is set as a right lung field reference point RB and a left pulmonary hilum is set as a left lung field reference point LB (see FIG. 5B). The pulmonary hilum is the portion which exists in almost the center portion of the inner side of the lung, and is where a bronchus, a pulmonary artery, and a pulmonary vein enter and exit the lung. In other words, the pulmonary hilum is the starting position of the blood vessel running and the blood vessel of the lung spreads from the pulmonary hilum toward the outline of the outer side of the lung field.

The reference point is set by, for example, displaying the reference image on the display unit 34 and setting a point which the user specified with the operation unit 33 on the reference image as the right lung field reference point RB and the left lung field reference point LB. Alternatively, a portion where blood vessels on the inner side of each lung field is concentrated can be extracted by image analysis from the reference image, and this portion can be acknowledged as the pulmonary hilum to be set as the reference point.

According to the present embodiment, a reference point is provided in each of the right lung field and the left lung field, but the reference point can be one point. For example, a position of a midpoint of a line connecting the right pulmonary hilum and the left pulmonary hilum can be set as the reference point.

Next, a distance from the reference point to the outline of the outer side of the lung field is calculated for each lung field (step S103). As shown in FIG. 5B, a distance from the right lung field reference point RB to the outline of the outer side of the right lung field (shown with a solid arrow in the right lung field of FIG. 5B) and a distance from the left lung field reference point LB to the outline of the outer side of the left lung field (shown with a solid arrow in the left lung field of FIG. 5B) are respectively calculated.

Next, the normalizing distance is set (step S104).

Figure 5C:
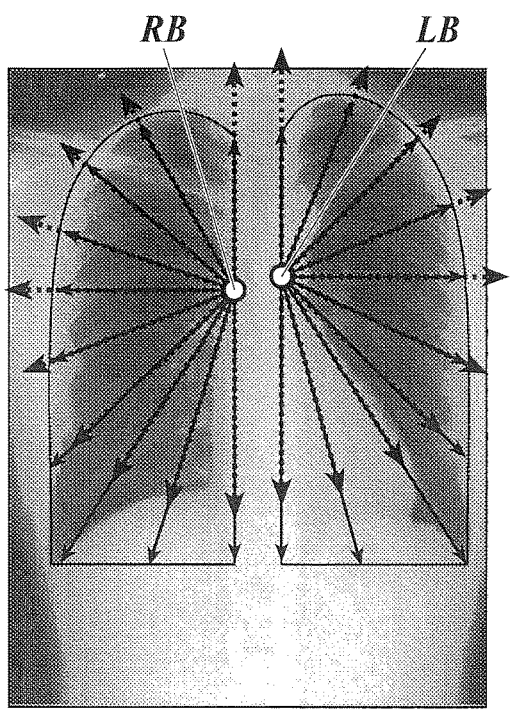
FIG. 5C is a diagram schematically showing a normalized lung field region.

Here, as shown in FIG. 5B, the distance from the reference point to the outline of the outer side of the lung field calculated in step S103 is different even within the same lung field depending on the position. Further, the distance is different between the left and the right lung fields. Therefore, in step S104, a distance (normalizing distance) to evenly normalize the distance from the reference point to the outline of the outer side of the lung field is set. FIG. 5C shows the normalizing distance with a dotted arrow. The normalizing distance is set to a predetermined constant value. Therefore, it is possible to suppress individual difference of shape and size of the lung field, and diagnosis by the physician and comparison with a later described comparison image becomes easy.

Next, the shape of the lung field region of the reference image is deformed based on the distance calculated in step S103 and the normalizing distance set in step S104 (step S105).

Specifically, in step S105, when the positions of the right lung field reference point RB and the left lung field reference point LB are misaligned in the vertical direction, the position of one reference point is matched to the position of the other reference point. Then, in each lung field, the lung field region is deformed so that the distance from the reference point to the outline of the outer side of the lung field is a certain normalizing distance. In other words, the image is enlarged or reduced so that a location where the distance from the reference point to the outline of the outer side of the lung field is shorter than the normalizing distance is extended to the normalizing distance and a location where the distance from the reference point to the outline of the outer side is longer than the normalizing distance is shortened to the normalizing distance. With this, the shape of the lung field region is deformed. Here, the range that each of the right lung field and the left lung field is deformed is within a range of 180 degrees above and below from the reference point.

Figure 5D:
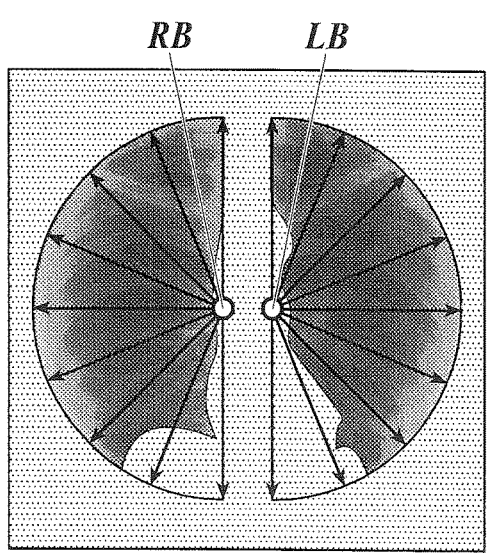
FIG. 5D is a diagram showing a deformed lung field region.

FIG. 5D shows an example of a reference image after deforming the shape of the lung field region. As shown in FIG. 5D, in the deformed reference image, the shape of the lung field region is deformed so that the outline of the outer side of each of the right lung field and the left lung field is a certain distance from the right lung field reference point RB and the left lung field reference point LB respectively. Therefore, as shown in FIG. 5D, the outline of the outer side of the lung field region is a circular arc shape. Although it is difficult to normalize the length of each one of the blood vessels in the lung field, by evening the distance from the pulmonary hilum to the outline of the outer side of the lung field to a certain distance, the length of the blood vessel in the lung field extending from the pulmonary hilum toward the outer side of the lung field is normalized simply. Since the lung field region is in a substantial semicircle shape with the pulmonary hilum as the center, the spread of the blood vessel from the pulmonary hilum is substantially in a radial shape. Therefore, it is possible to widen the space between the blood vessels in the locations where the distance from the pulmonary hilum to the outline is extended.

According to the present embodiment, the range of deforming each of the right lung field and the left lung field is set to a range of 180 degrees above and below from the reference point, and therefore each of the deformed lung field regions are substantially a semicircle. Alternatively, the range of deforming can be made smaller and the lung field region can be a fan shape. Alternatively, one reference point can be set as described above, and the lung field region can be deformed to be a circle. According to the present embodiment, the original frame image is a two dimensional image, however, when the original frame image is a three dimensional image, the lung field region is deformed to a hemisphere or a sphere.

After the deforming of the lung field region in the reference image ends, similar to deforming the lung field region in the reference image, the lung field regions in the plurality of other frame images are deformed (step S106), and the lung field region deforming processing ends.

Here, according to the present embodiment, capturing is performed in resting expiration. In an image captured in resting breathing, the misalignment of the position of the lung field region among the frame images due to breathing motion is slight. Therefore, considering the influence by such slight misalignment of the position and the influence of the increase in processing time and error due to performing well-known local matching processing and warping processing (See Japanese Patent Application Laid-Open Publication No. 2012-5729) to correct the misalignment of the position among the frame images, it is preferable to omit such processing (See Japanese Patent Application Laid-Open Publication No. 2012-110400). In step S106, the region in the same pixel position as the lung field region extracted from the reference image in step S101 is associated as the lung field region in the other frame images, and deformation similar to the reference image is performed.

In other words, the region in the same pixel position as the lung field region extracted in the reference image is extracted as the lung field region of the other frame images. The pixel position which is the same as the right lung field reference point RB and the left lung field reference point LB set in each of the left and right lung field of the reference image is set as the right lung field reference point RB and the left lung field reference point LB of the other frame images. The lung field regions of the other frame images are deformed so that the distance from the reference point to the outline on the outer side of the lung field is to be the normalizing distance. When the positions of the right lung field reference point RB and the left lung field reference point LB are aligned, similar alignment is performed.

Although the processing takes time, it is possible to align the corresponding positions of the lung fields between the reference image and the other frame images (positions illustrating the same structure in the lung field) by using well-known local matching processing and warping processing and then to perform the above lung field region deforming processing.

Returning to FIG. 3, when the lung field region deforming processing ends, the blood flow in the lung field region is analyzed and the blood flow analysis result image is generated based on the string of frame images with the lung field region deformed (step S12).

The blood flow analysis result image can be generated using any well-known method.

For example, Japanese Patent Application Laid-Open Publication No. 2012-5729 describes the following. The lung field region of each frame image is divided into small regions (for example, 2 mm×2 mm squares). High pass filter processing (for example, low pass cutoff frequency of 0.7 Hz) in a time axis direction is performed on each small region. A difference value of a representative value (average value, maximum value, etc.) of a signal value of each pixel in small regions in adjacent frame images is calculated to obtain an inter-frame difference image. This inter-frame difference image can be generated as the blood flow analysis result image. The inter-frame difference image is an image showing the inter-frame difference value of the small regions in adjacent frame images in each small region of the lung field region. In the inter-frame difference image generated by the above method, the signal change due to ventilation in each small range is removed, and the image shows the signal change due to blood flow in each small region.

Japanese Patent Application Laid-Open Publication No. 2012-239796 shows the following method. The lung field region of each frame image is divided into small regions. For each small region, the blood flow signal waveform is shifted in a unit of one frame with respect to the pulse signal waveform from the start of capturing (shifted in the time axis direction) to calculate the cross-correlation coefficient between the pulse signal waveform and the blood flow signal waveform. The image showing in each small region the maximum cross-correlation coefficient among the plurality of cross-correlation coefficient calculated by shifting a total of at least one cardiac cycle can be generated as the blood flow analysis result image.

The blood flow signal waveform can be derived by performing high pass filter processing (for example, low pass cutoff frequency 0.7 Hz) in the time axis direction for each small region of the string of frame images and then obtaining the waveform showing time change of the signal value.

Any of the following can be used as the pulse signal waveform.

(a) a waveform in which an ROI (region of interest) in a heart region (or aorta region) is defined and the waveform shows the time change of the signal value in the ROI (b) a signal waveform inverting the waveform of (a)

(c) an electrocardiographic signal waveform obtained by an electrocardiographic detecting sensor (d) a signal waveform showing a motion of a wall of the heart (change of position)

The cross-correlation coefficient can be derived from the following formula 1.

$$C = \frac{1}{J}\sum_{j=1}^{J} \frac{\{A(j) - m_A\}\{B(j) - m_B\}}{\sigma_A \sigma_B} \quad \text{[Formula 1]}$$

$$m_A = \frac{1}{J}\sum_{j=1}^{J} A(j),$$

$$m_B = \frac{1}{J}\sum_{j=1}^{J} B(j)$$

$$\sigma_A = \sqrt{\frac{1}{J}\sum_{j=1}^{J} \{A(j) - m_A\}^2}$$

$$\sigma_B = \sqrt{\frac{1}{J}\sum_{j=1}^{J} \{B(j) - m_B\}^2}$$

C: cross-correlation coefficient

A(j): j-th signal value among a total number of J signals included in pulse signal waveform $m_A$: average signal value of all signals included in pulse signal waveform $\sigma_A$: average deviation of all signals included in pulse signal waveform B(j): j-th signal value among a total number of J signals included in output signal waveform of small region $m_B$: average signal value of all signals included in output signal waveform of small region $\sigma_B$: average deviation of all signals included in output signal waveform of small region When the generating of the blood flow analysis result image ends, the display unit 34 displays operating buttons for selecting a use menu (1. display 2. analysis by region 3. comparison analysis) of the blood flow analysis result image, and when "1. display" is selected on the operation unit 33 (step S13; YES), the blood flow analysis result image is displayed on the display unit 34 (step S14).

For example, when the blood flow analysis result image is an inter-frame difference image, a color or a brightness value corresponding to the inter-frame difference value is assigned to each small region in each inter-frame difference image, and the above is displayed as a dynamic state image on the display unit 34 (sequentially displayed from the image with the smallest frame number). Alternatively, for each small region, the representative value such as the maximum value, the additional value, etc. of the inter-frame difference value in the string of inter-frame difference images is calculated, a color or brightness value corresponding to the calculated value is assigned to the corresponding small region in one of the inter-frame difference images, and the above is displayed on the display unit 34 (stationary image display).

Moreover, for example, when the blood flow analysis result image is an image from calculating the cross-correlation coefficient of the pulse signal waveform and the blood flow signal waveform, the color or the brightness value corresponding to the maximum value of the cross-correlation coefficient of each small region is assigned to each small region of the blood flow analysis result image and the above is displayed on the display unit 34. The blood flow analysis result image shows that the small region with the large value have a blood flow signal waveform close to the heart pulse signal waveform, in other words, there is sufficient blood flow.

Figure 6A:
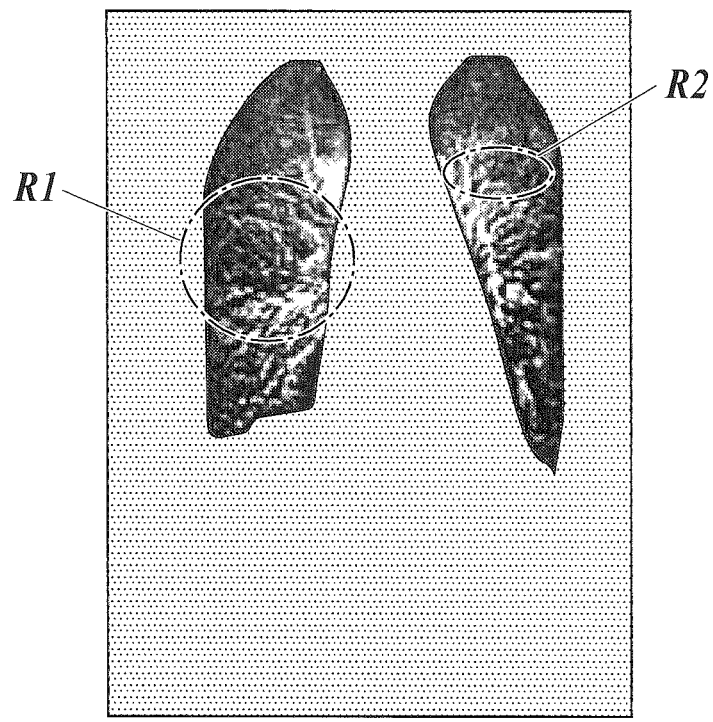
FIG. 6A is a diagram showing an example of a blood flow analysis result image generated without deforming the lung field region.
Figure 6B:
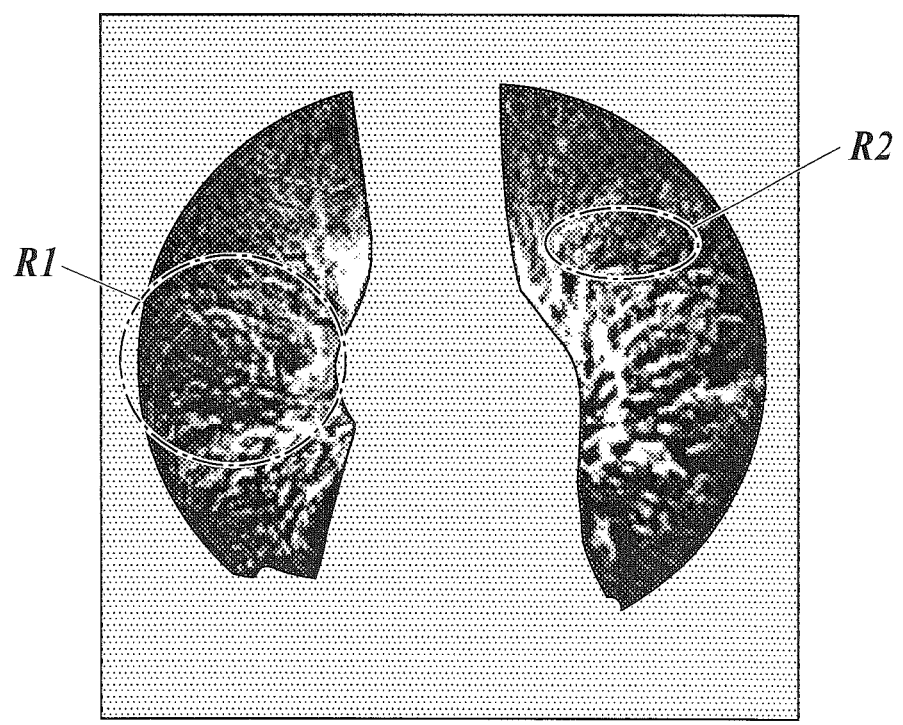
FIG. 6B is a diagram showing an example of a blood flow analysis result image generated after deforming the above lung field region.

FIG. 6A shows an example of a blood flow analysis result image generated without deforming the lung field region. FIG. 6B shows an example of a blood flow analysis result image generated after deforming the lung field region by the above described method. Both FIG. 6A and FIG. 6B are images in which the color or the brightness value according to the cross-correlation coefficient is assigned to the blood flow analysis result image from calculating the maximum value of the cross-correlation coefficient of each small region. FIG. 6A and FIG. 6B are generated based on the same string of frame images.

As shown in FIG. 6A, a large blood flow defect region (shown with R1 in FIG. 6A and FIG. 6B) can be confirmed by sight even in a blood flow analysis result image in which the lung field region is not deformed. However, a small blood flow defect region (shown with R2 in FIG. 6A and FIG. 6B) in a fine blood vessel portion where the blood vessels are running in an intricate network cannot be confirmed by sight in a blood flow analysis result image in which the lung field region is not deformed.

As shown in FIG. 6B, according to the blood flow analysis result image generated based on the lung field region deformed in the above described lung field deforming processing, in addition to being able to confirm by sight the large blood flow defect region R1, it is possible to confirm by sight the small blood flow defect region R2 which cannot be confirmed by sight in FIG. 6A. In the blood flow analysis result image shown in FIG. 6B, the lung field region is deformed to normalize the distance from the pulmonary hilum of each of the left and right lung field to the outline of the outer form of the lung field region. Therefore, the blood vessels are radially positioned from the pulmonary hilum which is the start of the blood vessel running toward the lung field, and the space between the blood vessels is enlarged in a location where the distance from the pulmonary hilum to the outline is extended. With this, the visibility of the intricate network of the blood vessels running can be enhanced, and the physician is able to easily acknowledge blood flow change or blood flow defect in the fine blood vessel portion such as peripheral portions which were difficult to be displayed in conventional blood flow analysis result images.

The dynamic state image of the thoracic portion is provided to the physician processed with the shape of the lung field normalized in the blood flow analysis result image as shown in FIG. 6B. Therefore, it is possible to provide the blood flow analysis result image with the individual difference of the shape of the lung field region, etc. suppressed. Consequently, diagnosis by the physician becomes easier. Further, comparison diagnosis with a past blood flow analysis result image of the same patient or a blood flow analysis result image of others becomes easier.

In step S14, together with the blood flow analysis result image, an index is displayed showing association of the value of the blood flow analysis result image (cross-correlation coefficient and inter-frame difference value) with the color and brightness value.

Returning to FIG. 3, when "2. analysis by region" is instructed on the operation unit 33 (step S13; NO, step S15; YES), an analysis target region according to the distance from the pulmonary hilum which is the reference point is set and the blood flow in the analysis target region is analyzed (step S16).

Setting the analysis target region according to the distance from the pulmonary hilum which is the reference point can be performed according to, for example, user operation of the operation unit 33. For example, the distance from the reference point to the outline of the outer side of the lung field region is to be blood vessel distance 100%, and the user sets and inputs on the operation unit 33 that a region of a blood vessel distance of a certain percent to another percent is to be the analysis target region. A plurality of analysis target regions can be set in one time.

The analysis of the blood flow in the analysis target region is performed using a value of the analysis result in each small region in the analysis target region of the blood flow analysis result image. For example, when the blood flow analysis result image is an inter-frame difference image, first, the representative value (maximum value, average value, etc.) of the inter-frame difference value of the small region included in the analysis target region in each inter-frame difference image is calculated as the inter-frame difference value in the analysis target region. Next, the representative value (maximum value, average value, etc.) of the inter-frame difference value of the analysis target region calculated from each inter-frame difference image is calculated. When the blood flow analysis result image is an image where the maximum value of the cross-correlation coefficient for each small region is calculated, the representative value (maximum value, minimum value, average value, additional value, etc.) of the maximum value of the cross-correlation coefficient of each small region in the analysis target region is calculated.

Then, the calculated analysis result of the blood flow in the analysis target region is displayed as the blood flow evaluation value in the analysis result screen 341 on the display unit 34 (step S17).

Figure 7:
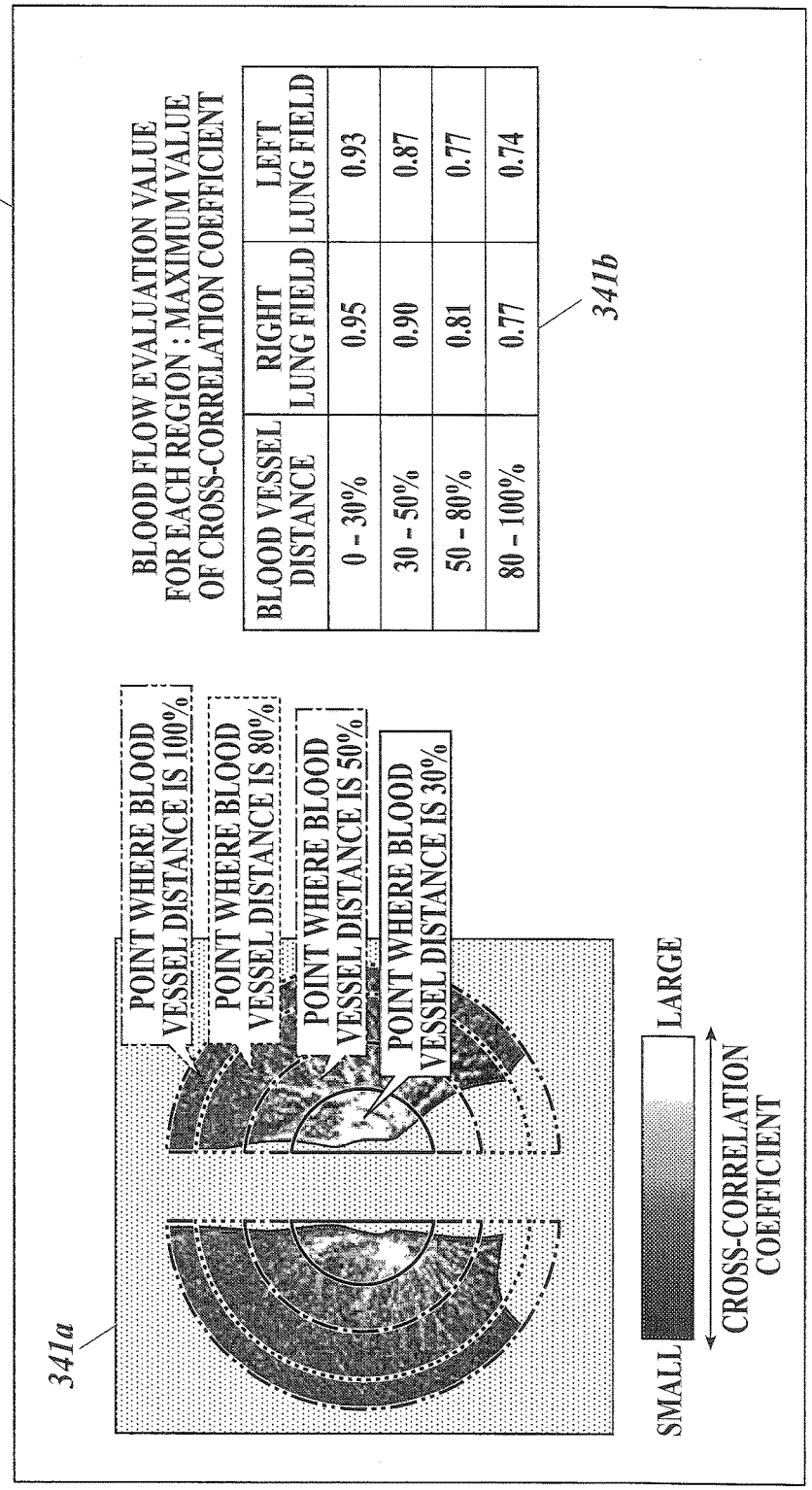
FIG. 7 is a diagram showing an example of an analysis result screen.

FIG. 7 shows an example of an analysis result screen 341 displayed in step S17. As shown in FIG. 7, an image display field 341a and a blood flow evaluation value display field 341b are provided in the analysis result screen 341 displayed in step S17. In the image display field 341a, an annotation showing the position of the analysis target region is displayed on the blood flow analysis result image displayed in a method similar to step S11 to step S12 of FIG. 3. In the blood flow evaluation value display field 341b, a result value of the analysis result of the blood flow in the analysis target region is displayed as the blood flow evaluation value. In FIG. 7, the average value of the maximum value of the cross-correlation coefficient is shown as an example of a blood flow evaluation value in each analysis target region.

According to the blood flow analysis result image generated in the present embodiment, the distance from the pulmonary hilum to the outline of the outer side of the lung field is normalized to be a certain distance and the length of the blood vessel in the lung field extending from the pulmonary hilum to the outer side of the lung field is also normalized simply. Therefore, the analysis of the blood flow by specifying the position of the blood vessel which has been conventionally difficult is made easy, examples of specifying the position including, setting the distance from the reference point to the outline of the outer side of the lung field region to be blood vessel distance 100% and setting a region of a blood vessel distance of a certain percent to another percent to be the analysis target region. Therefore, it is possible to provide a blood flow evaluation value which is diagnosis assistance information effective for diagnosis by the physician.

Returning to FIG. 3, when "3. comparison analysis" is instructed on the operation unit 33 (step S15; NO, step S18; YES), a difference image between the blood flow analysis result image generated this time and the comparison image is generated (step S19). Then, the difference value of the generated difference image is compared with the predetermined threshold value, the locations where the value exceeds the predetermined threshold value is extracted, and the image displaying the extracted locations with color so as to be identifiable is displayed in the comparison screen 342 on the display unit 34 (step S20).

Here, the comparison image is an image which is a comparison target to diagnose the present blood flow analysis result image. Examples of the comparison image include, a blood flow analysis result image of others (healthy person) with the same lung field region deformation and analysis as the blood flow analysis result image generated this time, a past blood flow analysis result image of the same patient, or the like. The comparison image is read out from the storage unit 32 according to specification by operating the operation unit 33.

The difference image is calculated by, for example, subtracting the analysis result value in the comparison image from the analysis result value (analysis result value of each small region) of the corresponding position in the blood flow analysis result image generated this time and calculating the difference value for each small region.

Figure 8:
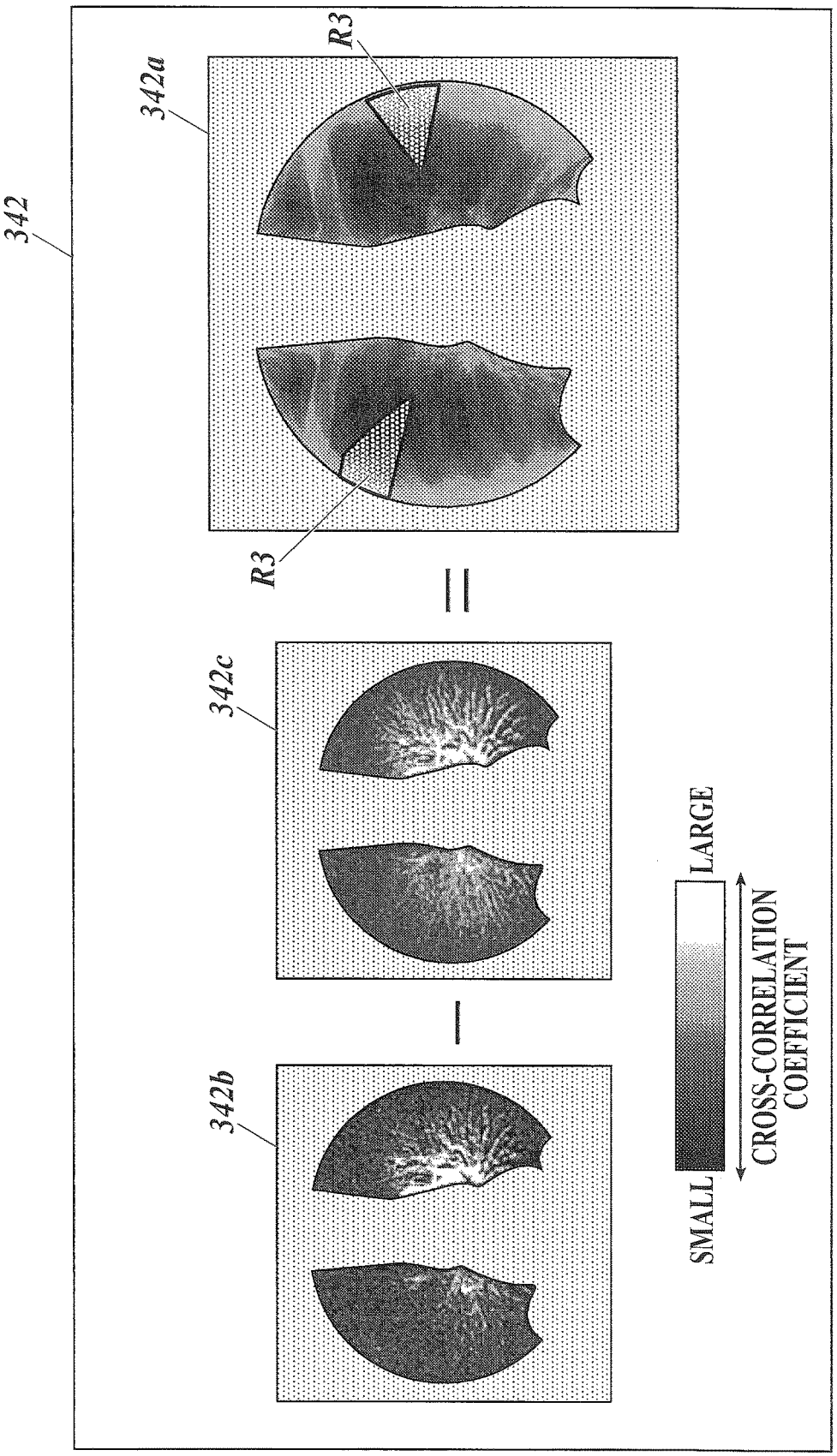
FIG. 8 is a diagram showing an example of a comparison screen.

FIG. 8 shows an example of a comparison screen 342 displayed in step S20.

As shown in FIG. 8, in comparison screen 342, the image 342a is displayed with the portion where the difference value exceeds the predetermined threshold value in the difference image displayed with an annotation such as color to be identifiable. The location shown with R3 in the image 342*a* is the region where the difference value is large. As shown in FIG. 8, the blood flow analysis result image 342*b* of the diagnosis target generated this time and the comparison image 342*c* are both displayed together with the image 342*a* so that the physician is able to refer to the images which are the basis of the difference image.

According to the blood flow analysis result image generated by the method of the present embodiment, the lung field shape is normalized so that the distance from the reference point to the outline of the outer side of the lung field region becomes a certain distance. Therefore, it is possible to suppress the difference due to individual difference in the shape or the running of the blood vessels in the lung field or the state of capturing, and comparison analysis with images of others (healthy person) or past images of the same patient becomes easy.

In step S20, the location where the difference value is a predetermined threshold value or less can be extracted and the extracted location can be displayed with annotation such as coloring to identifiably display the portion without change from the image of the healthy person or the past image of the same patient. In other words, by extracting at least one of the location where the difference value is larger than the predetermined threshold value or the location where the difference value is smaller than the predetermined threshold value, the physician is able to easily identify the portion where there is change or the portion where there is no change from the image of the healthy person or the past image of the same patient. Each small region of the lung field region of the difference image can be displayed with a color according to the difference value.

According to the present embodiment, the annotation showing the comparison analysis result is displayed on the deformed lung field region as shown in the image 342*a*, however, the annotation can be displayed on the lung field region before deforming. For example, the location where the difference value in the difference image generated in step S19 is larger or smaller than the predetermined threshold value can be extracted, the region corresponding to the extracted location can be specified on the blood flow analysis result image before deforming (or the frame image of the reference image, etc. before deforming), and the specified location can be displayed with annotation. Each region in the lung field region before deforming can be displayed with a color according to the difference value.

In the screen displaying the various images in step S14, step S17, and step S20, the above described use menu button and end button are displayed, and the user is able to instruct execute of other menus or end by operation on the operation unit 33.

Returning to FIG. 3, after display, it is judged whether end of the processing is instructed on the operation unit 33 (step S21). When it is judged that the end of the processing is not instructed (step S21; NO), the processing returns to step S13, and the processing of step S13 to step S21 is repeated. When it is judged that the end of processing is instructed on the operation unit 33 (step S21; YES), the blood flow analysis result image is stored associated with the patient information, examination target site, date, etc. in the storage unit 32 (step S22), and the image analysis processing A ends.

[Modification]

In the description of the first embodiment, first the shape of the lung field region of the string of frame images is deformed and then the blood flow analysis result image is generated. Alternatively, the blood flow analysis result image as shown in FIG. 6B can be obtained by generating the blood flow analysis result image based on the string of frame images and then deforming the lung field region in the blood flow analysis result image as described above.

Figure 9:
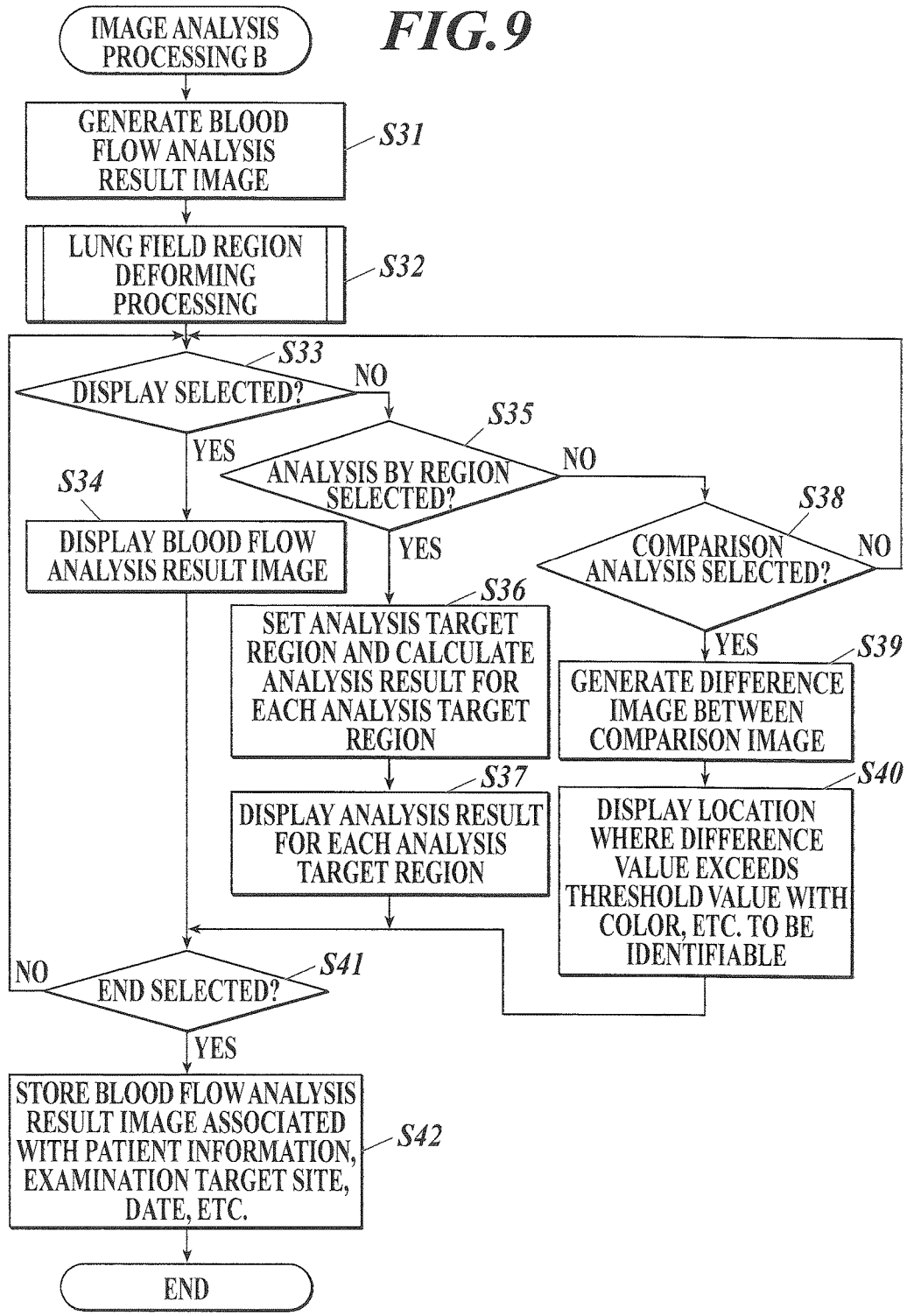
FIG. 9 is a flowchart showing image analysis processing B performed by the control unit of the diagnosis console shown in FIG. 1.

FIG. 9 shows a flowchart of an image analysis processing (image analysis processing B) in the modification. The image analysis processing B is executed by the control unit 31 in coordination with the program stored in the storage unit 32.

First, the string of frame images is analyzed, and the blood flow analysis result image is generated (step S31). In step S31, first, the lung field region is extracted from each frame image. Specifically, the lung field region is extracted from the reference image with the method described in step S101 of FIG. 4, and the region of the pixel position with the same position as the lung field region extracted in the reference image is extracted as the lung field region of the other frame images. Next, the analysis of the string of frame images is performed and the blood flow analysis result image is generated with the method illustrated in step S12 of FIG. 3.

Next, the lung field region deforming processing is performed on the lung field region of the generated blood flow analysis result image (step S32). The lung field region deforming processing performed in step S32 is similar to that in FIG. 4. However, since the lung field region is already extracted, the extracted result is used and the description is omitted here. According to step S31 to step S32, the blood flow analysis result image with the lung field region deformed as shown in FIG. 6B is obtained.

The processing of step S33 to step S42 are the same as the processing of the above described step S13 to step S22 of FIG. 3, and the description is incorporated herein.

As described above, even if the lung field region is deformed after generating the blood flow analysis result image, it is possible to generate the blood flow analysis result image with the lung field region deformed similar to the above described first embodiment and to perform display, analysis by region, comparison analysis, etc.

In the above description, the blood flow analysis result image with the lung field region deformed is described. Alternatively, it is possible to generate the ventilation analysis result image with the lung field region deformed.

As the ventilation analysis result image, for example, inspiration maximum air velocity image, expiration maximum air velocity image, maximum air velocity ratio image, etc. can be used.

The inspiration maximum air velocity image can be generated by the following. The lung field region is extracted from the string of frame images of at least one breathing cycle and divided into small regions. After performing low pass filter processing in the time axis direction for each small region, as described above, the difference value between the adjacent frames is calculated (the value with the smaller frame number is subtracted from the value with the larger frame number). The maximum value of the absolute value of the inter-frame difference value in the inspiration term (term that the inter-frame difference value is positive) is obtained to generate the image.

The expiration maximum air velocity image is obtained by the following. The lung field region is extracted from the string of frame images of at least one breathing cycle and divided into small regions. After performing low pass filter processing in the time axis direction for each small region, as described above, the difference value between the adjacent frames is calculated (the value with the smaller frame number is subtracted from the value with the larger frame number). The maximum value of the absolute value of the inter-frame difference value in the expiration term (term that the inter-frame difference value is negative) is obtained to generate the image.

The maximum air velocity ratio image can be generated by calculating the maximum value of the inter-frame difference value in the inspiration term/maximum value of the inter-frame difference value in the expiration term for each small region.

Figure 10A:
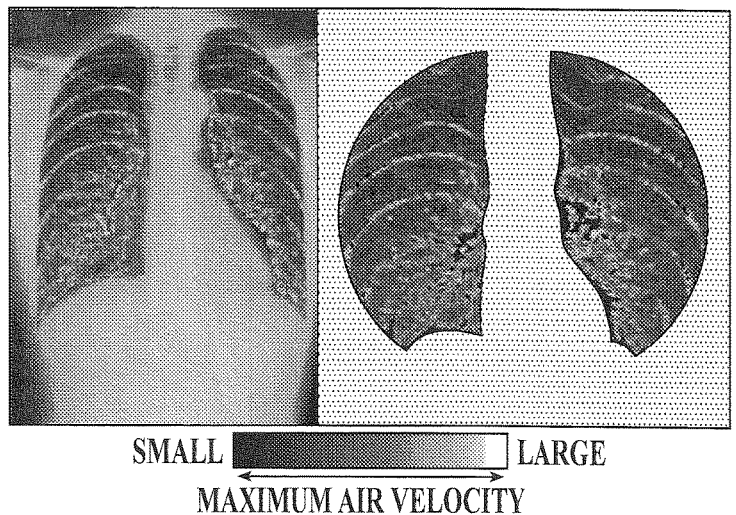
FIG. 10A is a diagram showing an example of a conventional inspiration maximum air velocity image and an example of an inspiration maximum air velocity image applying the present invention.
Figure 10B:
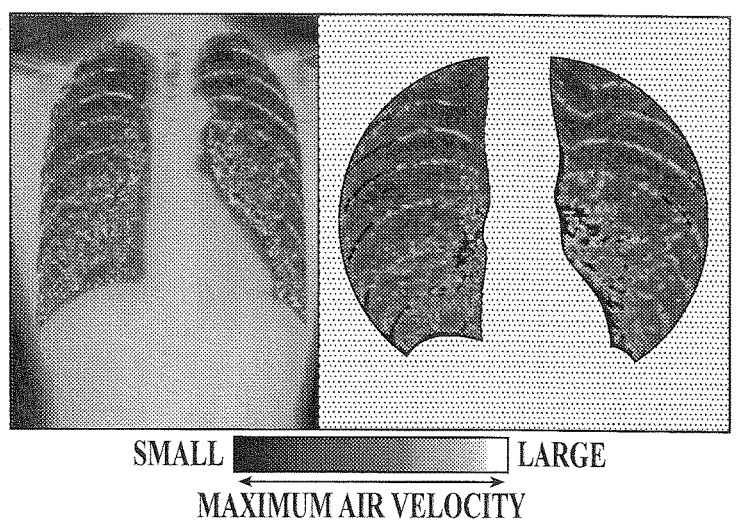
FIG. 10B is a diagram showing an example of a conventional expiration maximum air velocity image and an example of an expiration maximum air velocity image applying the present invention.
Figure 10C:
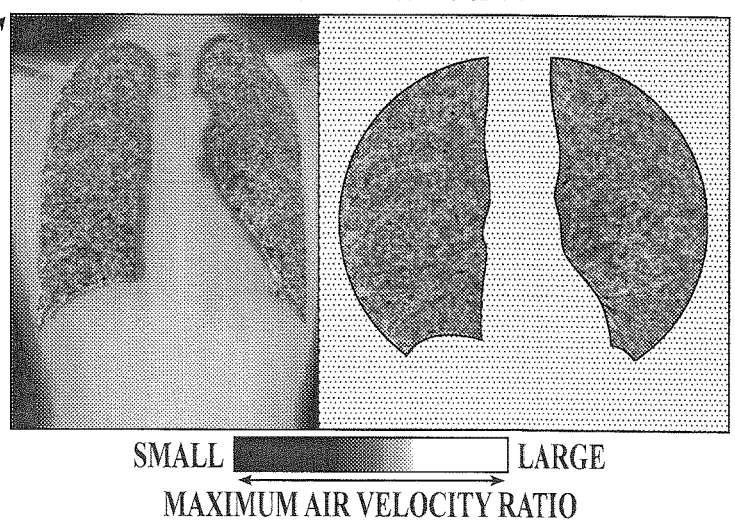
FIG. 10C is a diagram showing an example of a conventional maximum air velocity ratio image and an example of a maximum air velocity ratio image applying the present invention.

FIG. 10A shows an example of a conventional inspiration maximum air velocity image (left) and an inspiration maximum air velocity image (right) with the lung field region deformed by the method of the first embodiment or the modification. FIG. 10B shows an example of a conventional expiration maximum air velocity image (left) and an expiration maximum air velocity image (right) with the lung field region deformed by the method of the first embodiment or the modification. FIG. 10C shows an example of a conventional maximum air velocity ratio image (left) and a maximum air velocity ratio image (right) with the lung field region deformed by the method of the first embodiment or the modification. In FIG. 10A to FIG. 10C, coloring with a grayscale corresponding to the air velocity value and the air velocity ratio is shown. However, in the inspiration maximum air velocity image and the expiration maximum air velocity image shown in FIG. 10A and FIG. 10B, the value in the range of the upper 5% of the range of the possible air velocity value is considered to include more noise by the operation of the structure rather than information from breathing, and therefore the coloring is not applied (the portion can be observed with a black-like color in FIG. 10A and FIG. 10B).

In the ventilation analysis result image also, by deforming the lung field region so that the distance from the reference point to the outline of the outer side of the lung field becomes a certain distance by the method similar to the first embodiment or the modification, the difference in shape due to the individual difference or the state of capturing can be suppressed, and the analysis and diagnosis becomes easier.

As described above, according to the thoracic diagnosis assistance system 100, the control unit 31 of the diagnosis console 3 sets a reference point in the position corresponding to each other in the plurality of frame images generated by the capturing apparatus 1, extracts the lung field region from each of the plurality of frame images, and deforms the shape of the lung field region so that the distance from the set reference point to the outline of the outer side of the lung field region becomes a certain distance in each of the plurality of frame images. Then, analysis of dynamic state in the lung field region is performed based on the plurality of frame images with the shape of the lung field region deformed, and the analysis result image showing the analysis result in the corresponding position in the deformed lung field region is generated.

Alternatively, the control unit 31 analyzes the plurality of frame images generated by the capturing apparatus 1, generates the analysis result image, and deforms the lung field region of the generated analysis result image.

Therefore, since the analysis result image is generated by deforming the lung field region so that the distance from the reference point to the outline of the outer side of the lung field becomes a certain distance, it is possible to provide the analysis result image with the individual difference of the shape of the lung field region, etc. suppressed, and diagnosis by the physician becomes easier. Moreover, comparison diagnosis and comparison analysis with past analysis result image of the same patient or the analysis result image of others becomes easy.

For example, the blood flow analysis result image which analyzes the blood flow of the lung field is generated to make the diagnosis of blood flow in the lung field which has been difficult with conventional images easier for the physician. Moreover, comparison diagnosis and comparison analysis with past blood flow analysis result image of the same patient or the blood flow analysis result image of others becomes easy.

Moreover, since the reference point is set to the pulmonary hilum in the lung field region and the lung field region is deformed, the blood vessels are radially positioned from the pulmonary hilum which is the start point of the blood vessels running toward the lung field, and the space between the blood vessels becomes wider in the locations where the distance from the pulmonary hilum to the outline becomes long. Therefore, it is possible to enhance the visibility of the intricate network of the running blood vessels, and the physician is able to easily acknowledge blood flow change in the fine blood vessel portion such as peripheral portions or damage to the blood flow, which has been difficult from the conventional display of the blood flow analysis result image. Moreover, analysis according to distance of the pulmonary hilum to the blood vessel becomes possible.

The outline of the outer side of the lung field region is deformed to be an arc so that the analysis and diagnosis of the peripheral portions, etc., of the blood vessel becomes easy.

The color or brightness according to the value of the analysis result assigned in the lung field region of the analysis result image with the shape of the lung field region deformed is displayed on the display unit 34, and therefore, diagnosis by the physician can be made easier.

The analysis target region according to the distance from the reference point is set in the lung field region of the analysis result image with the shape of the lung field region deformed, and the analysis of the dynamic state in the set analysis target region is performed. Therefore, for example, in the analysis result image of the blood flow, it is possible to set the position of the blood vessel as the analysis target region based on the distance from the reference point which has been difficult in the past, and to perform effective analysis on the necessary region.

The difference value of the value of the analysis result in the corresponding positions of the two analysis result images with the shape of the lung field region deformed is calculated and the difference image is generated. In the difference image, at least one of the location with the difference value exceeding the predetermined threshold value or the location with the difference value equal to or lower than the predetermined threshold is extracted. Therefore, for example, the physician is easily able to acknowledge the region different from the past image of the same patient or the image of others (healthy person).

The analysis result image with the shape of the lung field region deformed is displayed on the display unit 34 with the diagnosis assistance information added. Therefore, diagnosis by the physician becomes much easier.

[Second Embodiment]

Next, the second embodiment of the present invention is described.

The second embodiment assists diagnosis for each blood vessel in the lung field.

The configuration of the thoracic diagnosis assistance system 100 and the operation of the capturing console 2 of the second embodiment is similar to those described in the first embodiment, and therefore the description is incorporated herein. According to the second embodiment, the operation of the image analysis processing is different from the first embodiment, and therefore is described below.

Figure 11:
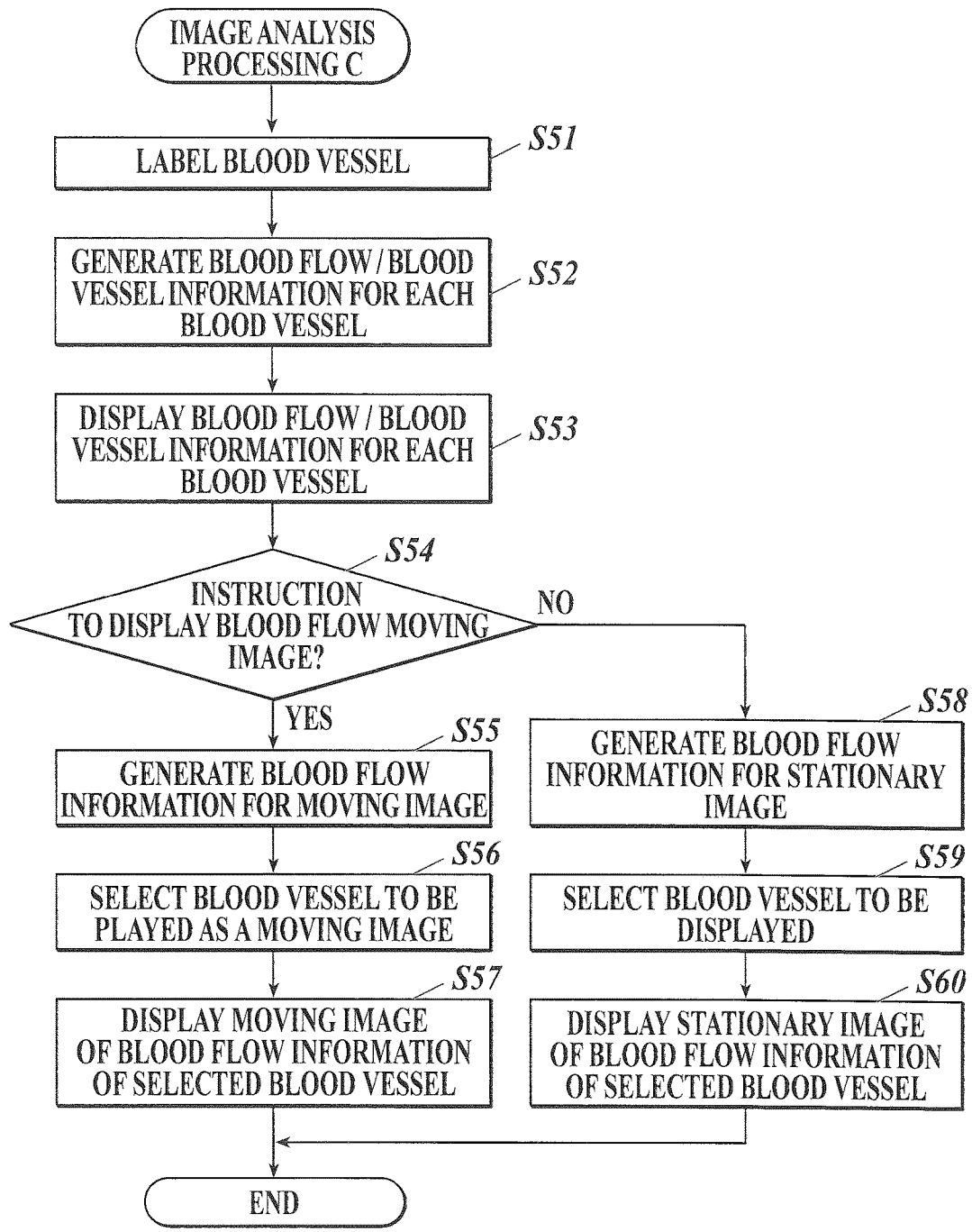
FIG. 11 is a flowchart showing image analysis processing C performed by the control unit of the diagnosis console shown in FIG. 1.

Below, the flow of the image analysis processing (image analysis processing C) is described with reference to FIG. 11. The image analysis processing C is executed by the control unit 31 in coordination with the program stored in the storage unit 32.

First, the blood vessel template image is used and the blood vessel of the lung field region is labeled in the string of frame images of the dynamic state image (step S51). The blood vessel template image is an image showing typical running of the blood vessel of the lung field region, and each blood vessel is labeled (labeled name is attached). The blood flow/blood vessel information of a healthy person is held for each blood vessel.

In step S51, first, the template matching of each blood vessel shape labeled in the blood vessel template image is performed with the reference image (for example, image resting expiratory level) among the string of frame images composing the dynamic state image and the region which matches with the blood vessel shape is labeled the same as this blood vessel. Next, the reference image is corresponded with the pixel in the same position in each frame image, and the position with the same position as the labeled blood vessel in the reference image is labeled as the position of this blood vessel in the other frame images. It is preferable that the resting expiratory level image is used as the reference image as described in the first embodiment. As described in the first embodiment, a plurality of frame images are corresponded by local matching and warping.

Figure 12:
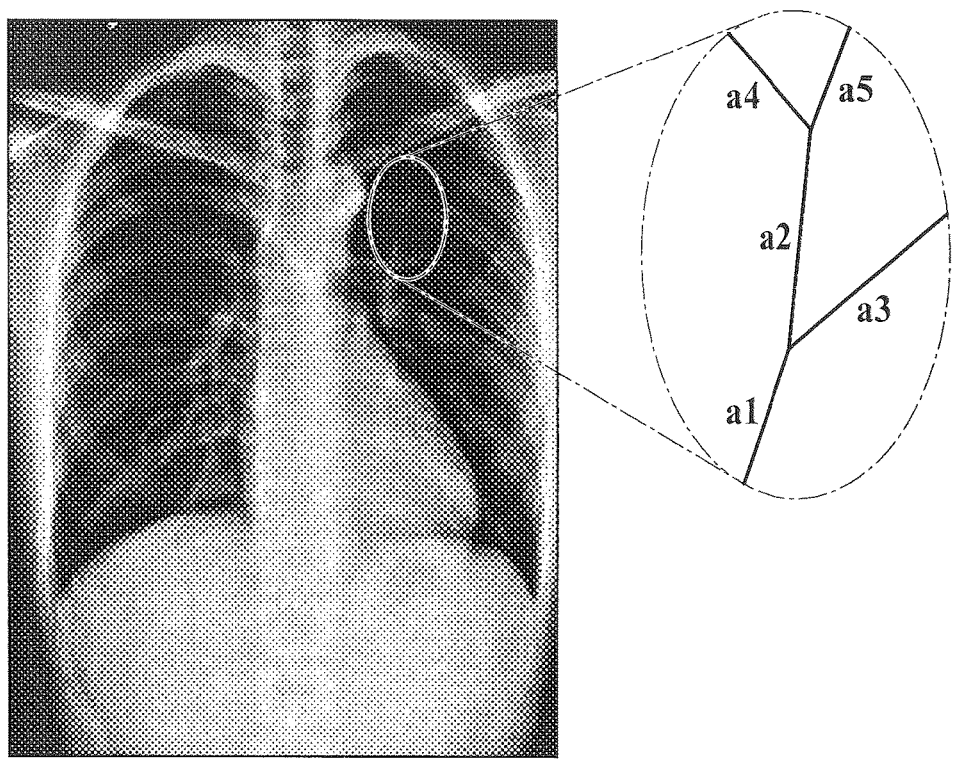
FIG. 12 is a diagram showing an example of labeling a blood vessel.

FIG. 12 shows an enlarged portion of a blood vessel labeled in the frame image. Reference numerals a1 to a5 show the labeled name. As shown in FIG. 12, a labeled name is provided for each vessel bifurcation.

Next, the blood flow/blood vessel information (blood flow or blood vessel information) for each blood vessel is generated based on the string of frame images with the blood vessel labeled (step S52).

For example, the following items (1) to (6) are extracted as the blood flow/blood vessel information.

(1) Blood Flow Amplitude Information

Figure 13A:
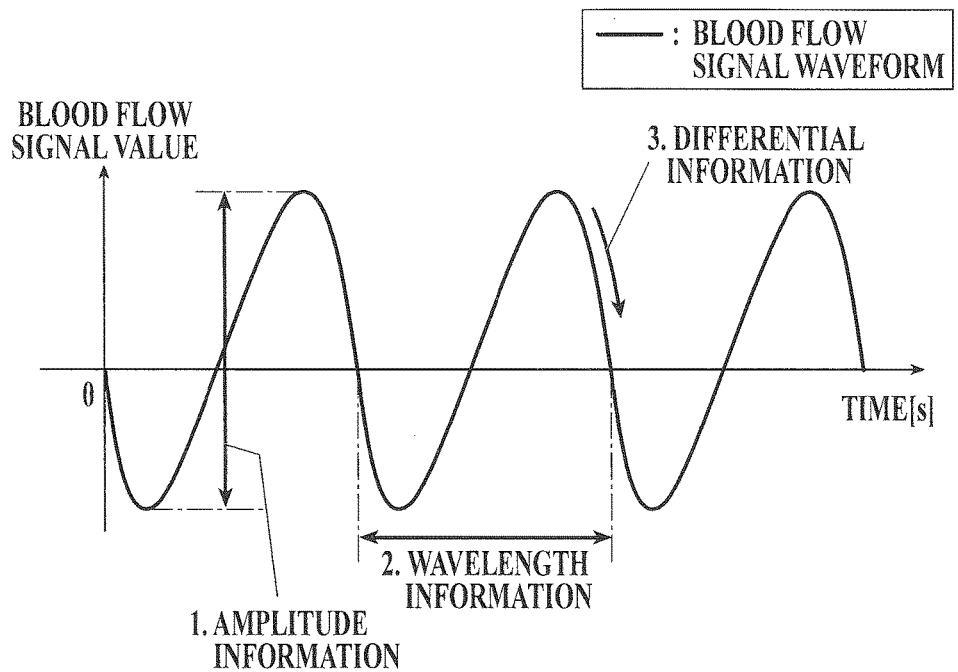
FIG. 13A is a diagram describing amplitude information of blood flow, wavelength information of blood flow and differential information of blood flow.

For example, the blood flow amplitude information can be obtained by, for example, generating a blood flow signal waveform for each blood vessel region, and subtracting a minimum signal value (local minimum value) from a maximum signal value (local maximum value) in a cardiac cycle of the blood flow signal waveform (see FIG. 13A). The blood flow signal waveform is a waveform showing a time change of a representative value (average value, maximum value, etc.) of a signal value on which the high pass filter processing in the time axis direction is performed.

(2) Blood Flow Wave Length Information

The blood flow wave length information can be obtained by, for example, generating a blood flow signal waveform for each blood vessel region, and obtaining a length (time) of one waveform cycle (see FIG. 13A).

(3) Blood Flow Differential Information (Maximum Differential Value Information)

The blood flow differential information can be calculated by obtaining the maximum value of the inter-frame difference value for each blood vessel region.

(4) Blood Flow Phase Information

Figure 13B:
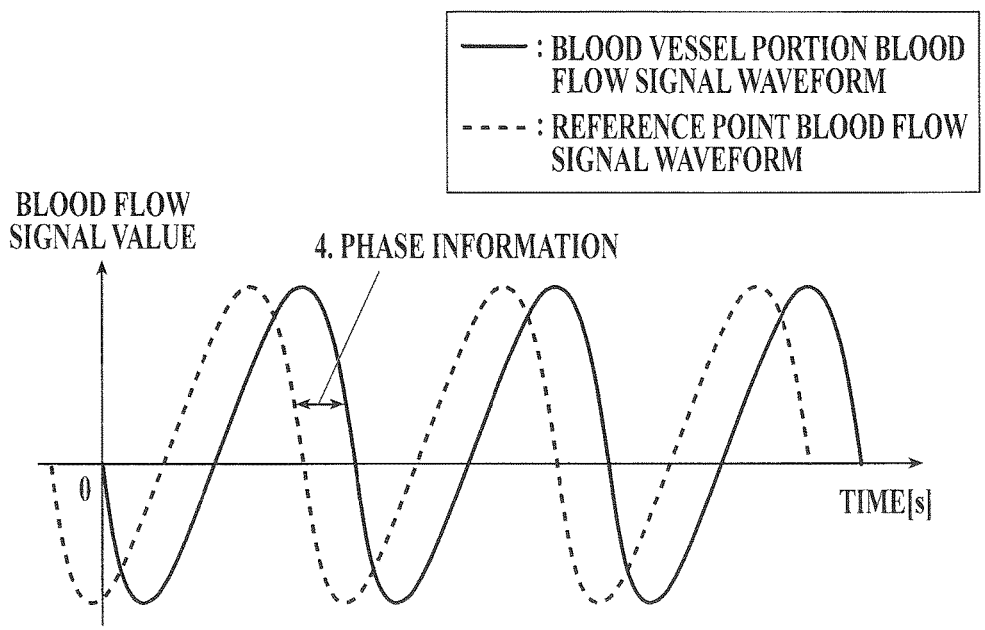
FIG. 13B is a diagram describing phase information of blood flow.

The blood flow phase information can be obtained by generating the blood flow signal waveform, and obtaining phase shift time from a waveform showing time change of the signal value in the reference point of the generated waveform (see FIG. 13B). For example, a point specified by the user on the operation unit 33 such as a heart right ventricle, a heart left ventricle, an aortic arch, etc., can be set as the reference point. If there is a specific blood vessel which the user desires to compare, the blood vessel can be specified as the reference point.

(5) Blood Vessel Shape Change Amount

The blood vessel shape change amount can be obtained by calculating the difference between a size of a blood vessel when there is blood flow and a size of a blood vessel when there is no blood flow for each blood vessel region. The point of the local minimum value of the blood flow signal waveform is specified as when there is blood flow and the point of the local maximum value of the blood flow signal waveform is specified as when there is no blood flow.

(6) Difference Information from Healthy Person

The difference information from the healthy person can be obtained by calculating the difference between the blood flow/blood vessel information of the items (1) to (5) obtained from the dynamic state image and the blood flow/blood vessel information of the healthy person.

Next, the blood flow/blood vessel information screen 343 for displaying the blood flow/blood vessel information for each blood vessel is displayed on the display unit 34 (step S53).

Figure 14:
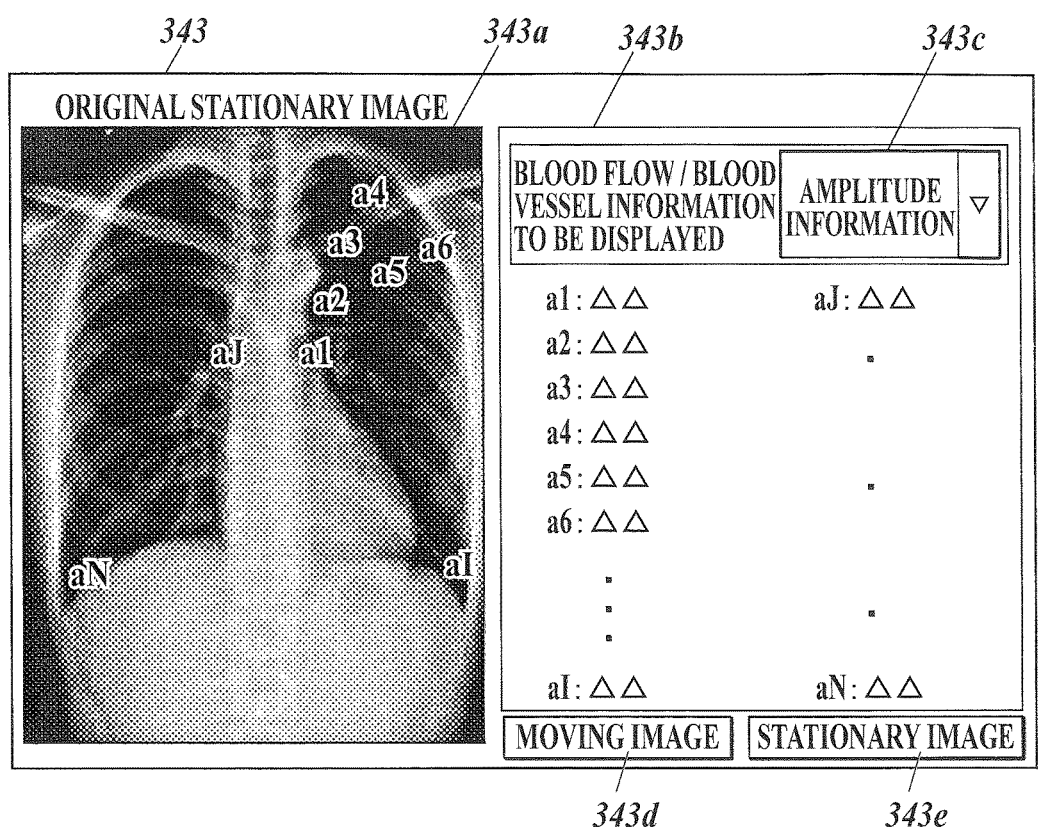
FIG. 14 is a diagram showing an example of a blood flow/blood vessel information display screen.

FIG. 14 shows an example of a blood flow/blood vessel information display screen 343 displayed on the display unit 34 in step S53. As shown in FIG. 14, an original image display field 343a, a blood flow/blood vessel information display field 343b, a pull down menu 343c, a dynamic image display button 343d, a stationary image display button 343e, and the like are provided in the blood flow/blood vessel information display screen 343. In the original image display field 343a, a frame among the string of frame images is displayed, and with this, the labeled name (a1 to aN) is displayed on the labeled blood vessel. In the blood flow/blood vessel information display field 343b, a value (shown with ΔΔ) of the blood flow/blood vessel information of each blood vessel is displayed associated with the labeled name of each blood vessel. The blood flow/blood vessel information displayed in the blood flow/blood vessel information display field 343b can be selected from the pull down menu 343c. In the original image display field 343a, the value of the blood flow/blood vessel information can be displayed together with the labeled name.

As described above, the position and the blood flow/blood vessel information of the labeled blood vessel are displayed as a list. Therefore, the physician is able to easily acknowledge the abnormal location of each blood vessel in the lung field region.

When the moving image display button 343d is pressed on the operation unit 33 and the display of the blood flow moving image is instructed (step S54; YES), the blood flow information for the moving image is generated for each blood vessel (step S55).

As the blood flow information, as described in step S12 of FIG. 3 in the first embodiment, for example, the inter-frame difference image in which the inter-frame difference value described in step S12 of FIG. 3 of the first embodiment is calculated is generated for each labeled blood vessel. Alternatively, the image in which the cross-correlation coefficient between the pulse signal waveform and the blood flow signal waveform is calculated while the blood flow signal waveform is shifted with respect to the pulse signal waveform one frame at a time (total shift amount being one cardiac cycle) can be generated for each labeled blood vessel and this can be the blood flow information.

Next, the moving image display screen 344 is displayed on the display unit 34 and the blood vessel which is played as the moving image is selected (step S56).

Figure 15:
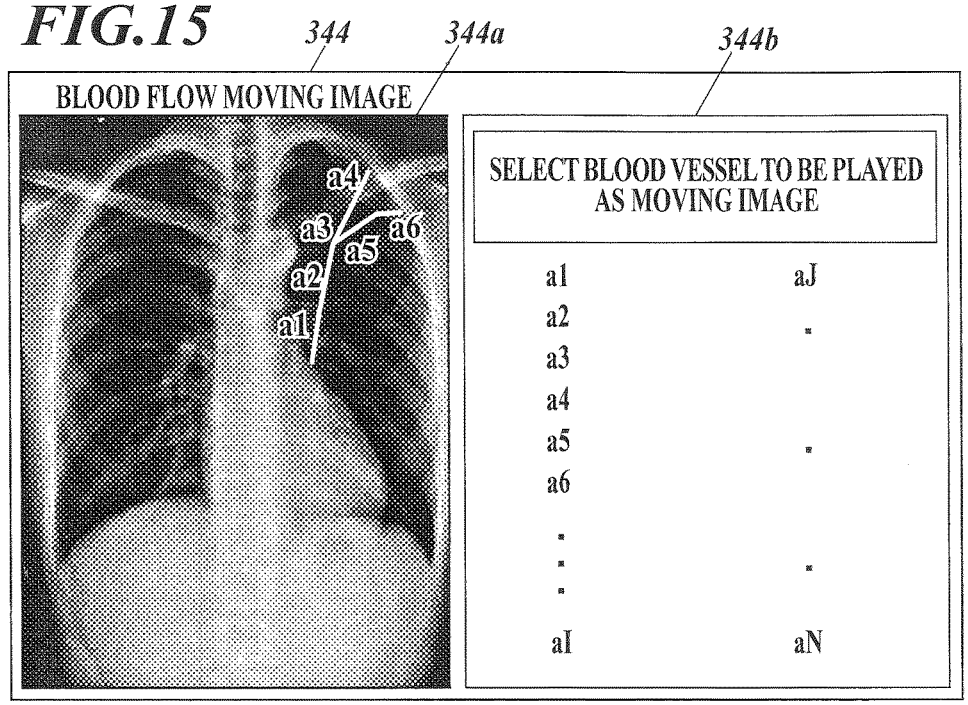
FIG. 15 is a diagram showing an example of a dynamic state image display screen.

FIG. 15 shows an example of the moving image display screen 344. As shown in FIG. 15, a blood flow moving image display field 344a and a blood vessel selection field 344b are provided in the moving image display screen 344.

The blood flow moving image of the selected blood vessel is displayed on the blood flow moving image display field 344a. A list of the labeled name of the blood vessel is displayed in the blood vessel selection field 344b, and the moving image of the blood vessel of the labeled name selected on the operation unit 33 from the list is displayed in the blood flow moving image display field 344a.

When the blood vessel of which the moving image is played is selected from the blood vessel selection field 344b on the operation unit 33, the blood flow information of the selected blood vessel is displayed in the blood flow moving image display field 344a of the moving image display screen 344 (step S57), and the image analysis processing C ends.

For example, when the blood flow information is the inter-frame difference image, the color or the brightness value corresponding to the inter-frame difference value of the selected blood vessel is assigned to the blood vessel region in each inter-frame difference image, and the image is displayed as a moving image on the display unit 34 (the inter-frame difference images are sequentially displayed starting from the image corresponding to the small frame number).

For example, when the blood flow information is an image in which the cross-correlation coefficient is calculated, the color (for example, the higher the cross-correlation coefficient, the redder the color, and the lower the cross-correlation coefficient, the blacker the color) or the brightness value corresponding to the cross-correlation coefficient of the selected blood vessel is assigned to the blood vessel region in each image, and the image is displayed as a moving image on the display unit 34 (the images are sequentially displayed starting from the image with the small shift amount).

As described above, the blood flow information of the selected blood vessel is displayed as a moving image. Therefore, for example, the physician is able to easily confirm the blood flow information of only the blood vessel which needs diagnosis, such as blood vessel where an abnormal value is found in the above described blood flow/blood vessel information display screen 343.

Alternatively, when the stationary image display button 343e is pressed on the operation unit 33 and the display of the blood flow stationary image is instructed (step S54; NO), the blood flow information for the stationary image is generated for each labeled blood vessel (step S58).

For example, as the blood flow information for the stationary image, for example, an MIP (Maximum Intensity Projection) of the cross-correlation coefficient for each labeled blood vessel is generated. The MIP is an image in which the maximum value is projected. The MIP can be created by generating the above described blood flow signal waveform for each labeled blood vessel, calculating the cross-correlation coefficient between the pulse signal waveform and the blood flow signal waveform while shifting the blood flow signal waveform with respect to the pulse signal waveform one frame at a time, and projecting the maximum cross-correlation coefficient for each blood vessel in which at least one cardiac cycle is shifted on the blood vessel corresponding to a frame image.

Next, the stationary image display screen 345 is displayed on the display unit 34 and the blood vessel to be displayed is selected (step S59).

Figure 16:
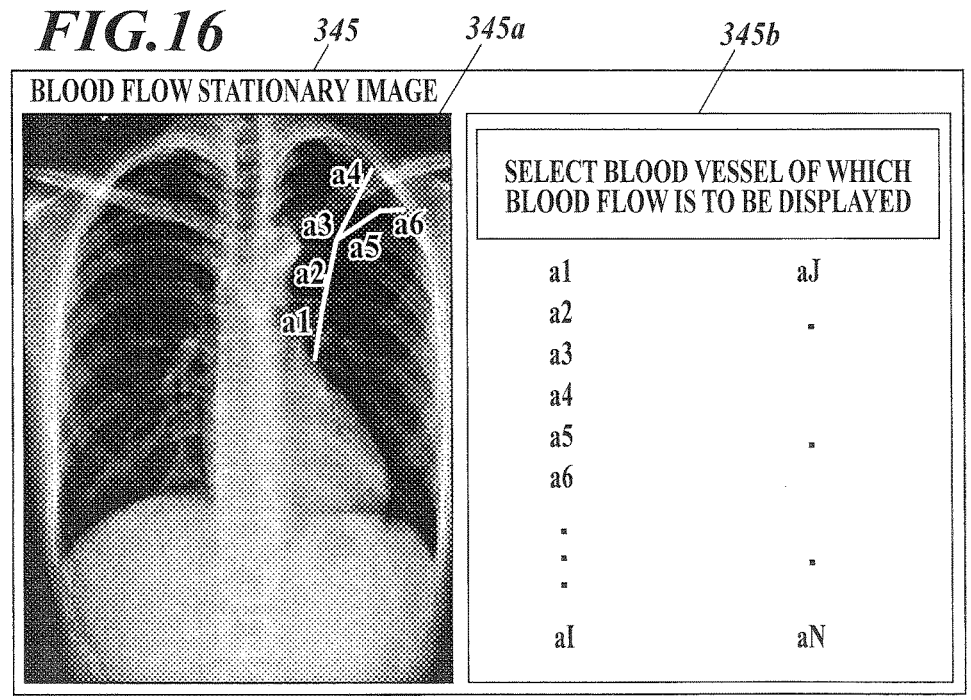
FIG. 16 is a diagram showing an example of a stationary image display screen.

FIG. 16 shows an example of the stationary image display screen 345. As shown in FIG. 16, the blood flow stationary image display field 345a and the blood vessel selection field 345b are provided in the stationary image display screen 345.

The blood flow stationary image of the selected blood vessel is displayed in the blood flow stationary image display field 345a. A list of the labeled name of the blood vessel is displayed in the blood vessel selection field 345b, and the stationary image of the blood vessel with the labeled name selected on the operation unit 35 from the list is displayed in the blood flow stationary image display field 345a.

When the blood vessel to be displayed is selected from the blood vessel selection field 345b on the operation unit 33, the blood flow information of the selected blood vessel is displayed in the blood flow stationary image display field 345a of the stationary image display screen 345 (step S60), and the image analysis processing C ends.

In step S60, for example, in the MIP, the color (for example, the higher the cross-correlation coefficient, the redder the color, and the lower the cross-correlation coefficient, the blacker the color) or the brightness value corresponding to the cross-correlation coefficient of the selected blood vessel is assigned to the region of this blood vessel and the MIP is displayed on the display unit 34.

As described above, the blood flow information of the selected blood vessel is displayed as a stationary image. Therefore, for example, the physician is able to easily confirm the blood flow information of only the blood vessel which needs diagnosis such as the blood vessel in which an abnormal value is found in the above described blood flow/blood vessel information display screen 343.

When the blood flow/blood vessel information, the blood flow moving image or the blood flow stationary image is displayed in the image analysis processing C, the above should be displayed after deforming the lung field region with the method described in the first embodiment. With this, the visibility of the blood vessel can be enhanced for the physician.

The first and second embodiment of the present invention describe an example of a preferable thoracic diagnosis assistance system of the present invention and the present invention is not limited to the above.

For example, the small region in the above embodiments is not limited to being composed from a plurality of pixels, and can be a region composed of a unit of one pixel.

For example, the above described description discloses an example using a hard disk, a nonvolatile memory, etc. as a computer readable medium of the program regarding the present invention, however, the present invention is not limited to the above example. As other computer readable mediums, it is possible to apply a portable storage medium such as a CD-ROM, etc. Moreover, as the medium providing data of the program regarding the present invention through the communication line, a carrier wave can be applied.

Other than the above, the detailed configuration and the detailed operation of each apparatus composing the thoracic diagnosis assistance system 100 can be suitably modified without leaving the scope of the present invention.

The entire disclosure of Japanese Patent Application No. 2013-176971 filed on Aug. 28, 2013 including description, claims, drawings, and abstract are incorporated herein by reference in its entirety.

What is claimed is:

1. A thoracic diagnosis assistance system comprising:
a capturing unit which captures a dynamic state of a thoracic portion to generate a plurality of frame images;
a deforming unit which sets a reference point in a position corresponding to each other among the plurality of generated frame images, extracts a lung field region from each of the plurality of frame images, and deforms a shape of the lung field region in each of the plurality of frame images so that a distance from the set reference point to an outline of an outer side of the lung field region becomes equal; and
a generating unit which analyzes a dynamic state in the lung field region based on the plurality of frame images in which a shape of the lung field region is deformed by the deforming unit, and generates an analysis result image showing a result of the analysis in a corresponding position in the deformed lung field region.

2. The thoracic diagnosis assistance system of claim 1, wherein, the generating unit analyzes blood flow in the lung field region, and generates an analysis result image showing an analysis result of the blood flow in a corresponding position in the lung field region.

3. The thoracic diagnosis assistance system of claim 1, wherein, the reference point is a pulmonary hilum in the lung field region.

4. The thoracic diagnosis assistance system of claim 1, wherein, the deforming unit deforms the shape of the lung field region so that the outline of the outer side of the lung field region is an arc shape.

5. The thoracic diagnosis assistance system of claim 1, further comprising, a display control unit which assigns a color or a brightness according to a value of the analysis result in the lung field region of the analysis result image with the shape of the lung field region deformed and displays the analysis result image on a display unit.

6. The thoracic diagnosis assistance system of claim 1, further comprising, a region analysis unit which sets an analysis target region according to a distance from the reference point, the analysis target region set in the lung field region in the analysis result image with the shape of the lung field region deformed, and analyzes the dynamic state in the set analysis target region.

7. The thoracic diagnosis assistance system of claim 1, further comprising,
a difference image generating unit which calculates a difference value between values of an analysis result of corresponding positions in two analysis result images with the shape of the lung field region deformed, and generates a difference image; and
an extracting unit which extracts at least one of a location in which the difference value exceeds a predetermined threshold value or a location in which the difference value is equal to or less than the predetermined threshold value in the difference image.

8. The thoracic diagnosis assistance system of claim 5, wherein, the display control unit displays on the display unit the analysis result image with the shape of the lung field region deformed including diagnosis assistance information.

9. A thoracic diagnosis assistance system comprising:
a capturing unit which captures a dynamic state of a thoracic portion to generate a plurality of frame images;
a generating unit which extracts a lung field region from the plurality of generated frame images, analyzes a dynamic state in the lung field region, and generates an analysis result image showing a result of the analysis in a corresponding position in the lung field region; and
a deforming unit which sets a reference point in the analysis result image, and deforms a shape of the lung field region in the analysis result image so that a distance from the set reference point to an outline of an outer side of the lung field region in the analysis result image becomes equal.

10. The thoracic diagnosis assistance system of claim 9, wherein, the generating unit analyzes blood flow in the lung field region, and generates an analysis result image showing an analysis result of the blood flow in a corresponding position in the lung field region.

11. The thoracic diagnosis assistance system of claim 9, wherein, the reference point is a pulmonary hilum in the lung field region.

12. The thoracic diagnosis assistance system of claim 9, wherein, the deforming unit deforms the shape of the lung field region so that the outline of the outer side of the lung field region is an arc shape.

13. The thoracic diagnosis assistance system of claim 9, further comprising, a display control unit which assigns a color or a brightness according to a value of the analysis result in the lung field region of the analysis result image with the shape of the lung field region deformed and displays the analysis result image on a display unit.

14. The thoracic diagnosis assistance system of claim 9, further comprising, a region analysis unit which sets an analysis target region according to a distance from the reference point, the analysis target region set in the lung field region in the analysis result image with the shape of the lung field region deformed, and analyzes the dynamic state in the set analysis target region.

15. The thoracic diagnosis assistance system of claim 9, further comprising,
a difference image generating unit which calculates a difference value between values of an analysis result of corresponding positions in two analysis result images with the shape of the lung field region deformed, and generates a difference image; and
an extracting unit which extracts at least one of a location in which the difference value exceeds a predetermined threshold value or a location in which the difference value is equal to or less than the predetermined threshold value in the difference image.

16. The thoracic diagnosis assistance system of claim 13, wherein, the display control unit displays on the display unit the analysis result image with the shape of the lung field region deformed including diagnosis assistance information.

* * * * *